US012622956B2

(12) United States Patent
McCurry et al.

(10) Patent No.: US 12,622,956 B2
(45) Date of Patent: *May 12, 2026

(54) METHODS AND VACCINES FOR INDUCING IMMUNE RESPONSES TO MULTIPLE DIFFERENT MHC MOLECULES

(71) Applicants: Mayo Foundation for Medical Education and Research, Rochester, MN (US); University of Washington, Seattle, WA (US)

(72) Inventors: Dustin B. McCurry, Phoenix, AZ (US); Peter A. Cohen, Scottsdale, AZ (US); Latha B. Pathangey, Scottsdale, AZ (US); Sandra J. Gendler, Scottsdale, AZ (US); Mary L Disis, Renton, WA (US)

(73) Assignees: Mayo Foundation for Medical Education and Research;, Rochester (MN); University of Washington, Seattle, WA (US)

( * ) Notice: Subject to any disclaimer, the term of this patent is extended or adjusted under 35 U.S.C. 154(b) by 881 days.

This patent is subject to a terminal disclaimer.

(21) Appl. No.: 17/822,051

(22) Filed: Aug. 24, 2022

(65) Prior Publication Data

US 2023/0098624 A1     Mar. 30, 2023

Related U.S. Application Data

(63) Continuation of application No. 15/781,393, filed as application No. PCT/US2016/064749 on Dec. 2, 2016, now Pat. No. 11,464,839.

(60) Provisional application No. 62/263,256, filed on Dec. 4, 2015.

(51) Int. Cl.
| | |
|---|---|
| *A61K 39/00* | (2006.01) |
| *A61K 39/12* | (2006.01) |
| *A61K 39/245* | (2006.01) |
| *A61K 39/39* | (2006.01) |
| *A61K 40/11* | (2025.01) |
| *A61K 40/42* | (2025.01) |
| *A61K 40/46* | (2025.01) |
| *A61P 35/02* | (2006.01) |
| *C07K 14/005* | (2006.01) |
| *C07K 16/00* | (2006.01) |

(52) U.S. Cl.
CPC .... *A61K 39/00117* (2018.08); *A61K 39/0011* (2013.01); *A61K 39/001106* (2018.08); *A61K 39/001114* (2018.08); *A61K 39/001168* (2018.08); *A61K 39/001184* (2018.08); *A61K 39/12* (2013.01); *A61K 39/245* (2013.01); *A61K 39/39* (2013.01); *A61K 40/11* (2025.01); *A61K 40/4205* (2025.01); *A61K 40/4257* (2025.01); *A61K 40/46* (2025.01); *A61P 35/02* (2018.01); *C07K 14/005* (2013.01); *C07K*

*16/00* (2013.01); *A61K 2039/55505* (2013.01); *A61K 2039/55511* (2013.01); *A61K 2039/55561* (2013.01); *A61K 2039/55566* (2013.01); *A61K 2039/55572* (2013.01); *A61K 2239/49* (2023.05); *C12N 2710/16122* (2013.01); *C12N 2710/16134* (2013.01)

(58) Field of Classification Search
CPC ...... A61K 39/00117; A61K 39/001168; A61K 39/001106; A61K 39/001184; A61K 39/245; A61K 2039/55511; A61K 2039/55505; A61K 40/11
See application file for complete search history.

(56) References Cited

U.S. PATENT DOCUMENTS

| | | | |
|---|---|---|---|
| 6,548,643 B1 | 4/2003 | McKenzie et al. | |
| 6,734,172 B2 | 5/2004 | Scholler et al. | |
| 7,202,346 B2 | 4/2007 | Payne et al. | |
| 7,524,503 B2 | 4/2009 | Khanna et al. | |
| 7,659,117 B2 | 2/2010 | Laus et al. | |
| 7,820,786 B2 | 10/2010 | Thomson et al. | |
| 7,935,804 B2 | 5/2011 | Dubensky, Jr. et al. | |
| 8,815,249 B2 | 8/2014 | Humphreys et al. | |
| 8,951,526 B2 | 2/2015 | Yonezawa | |
| 11,464,839 B2 | 10/2022 | McCurry et al. | |
| 2004/0101534 A1 | 5/2004 | Diamond | |
| 2009/0274714 A1* | 11/2009 | Singh ..................... | A61P 37/02 435/375 |

(Continued)

FOREIGN PATENT DOCUMENTS

| | | |
|---|---|---|
| WO | WO 2001/074855 | 10/2001 |
| WO | WO 2001/082963 | 11/2001 |

(Continued)

OTHER PUBLICATIONS

Nielsen et al (PLoS Computational Biology, 2008, vol. 4, No. 7, e1000107, 10 pages) (Year: 2008).*

(Continued)

*Primary Examiner* — Karen A. Canella
(74) *Attorney, Agent, or Firm* — Fish & Richardson P.C.

(57) ABSTRACT

This document provides methods and materials relating to isolated polypeptides, polypeptide preparations, vaccine preparations (e.g., anti-cancer vaccine preparations), and methods for vaccinating mammals. For example, polypeptides (e.g., CMV, MUC1, HER2, Mesothelin (MESO), TRAG-3, or CALR polypeptides) having the ability to be processed into different polypeptides such that the processed polypeptides as a group are capable of being presented by different MHC molecules present in a particular mammalian population are provided.

32 Claims, 10 Drawing Sheets

Specification includes a Sequence Listing.

(56) References Cited

U.S. PATENT DOCUMENTS

| 2012/0308513 A1 | 12/2012 | Wollan et al. |
| 2013/0011424 A1 | 1/2013 | Maksyutov et al. |
| 2013/0011426 A1 | 1/2013 | Tureci et al. |
| 2013/0028915 A1 | 1/2013 | Palucka et al. |
| 2013/0108657 A1 | 5/2013 | Yee et al. |
| 2013/0203163 A1 | 8/2013 | Wollan et al. |
| 2014/0286858 A1 | 9/2014 | Zimmerman et al. |
| 2014/0356318 A1* | 12/2014 | Barken ............. A61K 38/1841 |
| | | 435/375 |
| 2015/0196628 A1 | 7/2015 | Mason et al. |
| 2019/0000948 A1 | 1/2019 | McCurry et al. |

FOREIGN PATENT DOCUMENTS

| WO | WO 2005/049072 | 6/2005 | |
| WO | WO 2006/056027 | 6/2006 | |
| WO | WO 2009/059011 | 5/2009 | |
| WO | WO 2009/155535 | 12/2009 | |
| WO | WO 2011/110953 | 9/2011 | |
| WO | WO 2012/038055 | 3/2012 | |
| WO | WO 2013/025972 | 2/2013 | |
| WO | WO 2015/033140 | 3/2015 | |
| WO | WO 2015/100360 | 7/2015 | |
| WO | WO2015/157189 | * 10/2015 | ............. A61K 39/12 |
| WO | WO 2017/034833 | 3/2017 | |

OTHER PUBLICATIONS

Abstract of Rughetti et al.(Blood, 2008, vol. 112, p. 5237) (Year: 2008).
Ackerman et al., "A role for the endoplasmic reticulum protein retrotranslocation machinery during crosspresentation by dendritic cells," Immunity, Oct. 2006, 25(4):607-617.
Ackerman et al., "Early phagosomes in dendritic cells form a cellular compartment sufficient for cross presentation of exogenous antigens," Proc. Natl. Acad. Sci. USA, Oct. 28, 2003, 100(22):12889-12894.
Akiyama et al., "Identification of HLA-A24-restricted CTL epitope encoded by the matrix protein pp65 of human cytomegalovirus," Immunol. Lett., Aug. 2002, 83(1):21-30.
Alves et al., "Differential regulation of human IL-7 receptor alpha expression by IL-7 and TCR signaling," J. Immunology, Apr. 15, 2008, 180(8):5201-5210.
Apostolopoulos et al., "A glycopeptide in complex with MHC class I uses the GalNAc residue as an anchor," Proc. Natl. Acad. Sci. USA, Dec. 1, 2003, 100(25):15029-15034.
Arentz-Hansen et al., "Celiac lesion T cells recognize epitopes that cluster in regions of gliadins rich in proline residues," Gastroenterology, Sep. 2002, 123(3):803- 809.
Belizaire et al., "Targeting proteins to distinct subcellular compartments reveals unique requirements for MHC class I and II presentation," Proc. Natl. Acad. Sci. USA, Oct. 13, 2009, 106(41):17463-17468.
Belyakov et al., "Mucosal immunization with HIV-1 peptide vaccine induces mucosal and systemic cytotoxic T lymphocytes and protective immunity in mice against intrarectal recombinant HIV-vaccinia challenge," Proc. Natl. Acad. Sci. U.S.A., Feb. 1998, 95(4):1709-1714.
Brinckerhoff et al., "Terminal modifications inhibit proteolytic degradation of an immunogenic MART-1(27-35) peptide: implications for peptide vaccines," Int. J. Cancer, Oct. 1999, 83(3):326-34.
Caserta et al., "IL-7 is superior to IL-2 for ex vivo expansion of tumour-specific CD4(+) T cells," Eur. J. Immunology, Feb. 2010, 40(2):470-479.
Chhabra et al., The Scientific World Journal, 2011, vol. 11, pp. 121-129 (Year: 2011).
Cieri et al., "IL-7 and IL-15 instruct the generation of human memory stem T cells from naive precursors," Blood, Jan. 24, 2013, 121(4):573-584.

Cohen et al., "CD4+ T cells in adoptive immunotherapy and the indirect mechanism of tumor rejection," Crit. Rev. Immunology, 2000, 20(1):17-56.
Cohen et al., "STAT3- and STAT5-dependent pathways competitively regulate the pan-differentiation of CD34pos cells into tumor-competent dendritic cells," Blood, Sep. 1, 2008, 112(5):1832-1843.
Cohen et al., "T-cell adoptive therapy of tumors: Mechanisms of improved therapeutic performance," Crit. Rev. Immunology, 2001, 21(1-3):215-248.
Crespo et al., "TLR7 triggering with polyuridylic acid promotes cross-presentation in CD8alpha+ conventional dendritic cells by enhancing antigen preservation and MHC class I antigen permanence on the dendritic cell surface," J. Immunology, Feb. 2013, 190(3):948-960.
Delamarre et al., "Presentation of exogenous antigens on major histocompatibility complex (MHC) class I and MHC class II molecules is differentially regulated during dendritic cell maturation," J. Exp. Medicine, Jul. 7, 2003, 198(1):111-122.
Deshpande et al., "IL-7- and IL-15-mediated TCR sensitization enables T cell responses to self-antigens," J. Immunology, Feb. 15, 2013, 190(4):1416-1423.
Di Genova et al., "Bystander stimulation of activated CD4+ T cells of unrelated specificity following a booster vaccination with tetanus toxoid," Eur. J. Immunology, Apr. 2010, 40(4):976-985.
Disis et al., "Concurrent Trastuzumab and HER2/neu-Specific Vaccination in Patients With Metastatic Breast Cancer," J. Clin. Oncology, 27(28): 4685-4692.
Disis et al., "Generation of T-cell immunity to the HER-2/neu protein after active immunization with HER-2/neu peptide-based vaccines," J. Clin. Oncology, Jun. 1, 2002, 20(11):2624-2632.
Disis et al., "HER-2/neu vaccine-primed autologous T-cell infusions for the treatment of advanced stage HER-2/neu expressing cancers," Cancer Immunol. Immunotherapy, Feb. 2014, 63(2):101-109.
Dudley et al., "Adoptive cell transfer therapy following non-myeloablative but lymphodepleting chemotherapy for the treatment of patients with refractory metastatic melanoma," J. Clin. Oncology, Apr. 1, 2005, 23(10):2346-2357.
Dudley et al., "Cancer regression and autoimmunity in patients after clonal repopulation with antitumor lymphocytes," Science, Oct. 25, 2002, 298(5594):850-854.
Dudley et al., "Randomized selection design trial evaluating CD8+-enriched versus unselected tumor-infiltrating lymphocytes for adoptive cell therapy for patients with melanoma," J. Clin. Oncology, Jun. 10, 2013, 31(17):2152-2159.
European Search Report in European Application No. 16871630.6 dated Jul. 16, 2019, 16 pages.
European Search Report in European Application No. 16871630.6 dated Oct. 28, 2019, 10 pages.
Faure et al., "Long-lasting cross-presentation of tumor antigen in human DC," Eur. J. Immunology, Feb. 2009, 39(2):380-390.
Fraser et al., "Generation of a universal CD4 memory T cell recall peptide effective in humans, mice and non-human primates," Vaccine, May 19, 2014, 32(24):2896-2903.
Gagnon et al., "Increased antigen responsiveness of naive CD8 T cells exposed to IL-7 and IL-21 is associated with decreased CD5 expression," Immunol. Cell Biology, May-Jun. 2010, 88(4):451-460.
Garulli et al., "Primary CD8+ T-cell response to soluble ovalbumin is improved by chloroquine treatment in vivo," Clin. Vaccine Immunology, Oct. 2008, 15(10):1497-1504.
Gragert et al., "Six-locus high resolution HLA haplotype frequencies derived from mixed-resolution DNA typing for the entire US donor registry," Hum. Immunology, Oct. 2013, 74(10):1313-1320.
Hattrup et al., "Structure and function of the cell surface (tethered) mucins," Annu. Rev. Physiology, 2008, 70:431-457.
Hertz et al., "HIV-1 Vaccine-Induced T-Cell Reponses Cluster in Epitope Hotspots that Differ from Those Induced in Natural Infection with HIV-1," PLoS Pathogens, Jun. 20, 2013, 9(6):e1003404, 14 pages.
Heukamp et al., "Identification of three non-VNTR MUC1-derived HLA-A*0201-restricted T-cell epitopes that induce protective anti-tumor immunity in HLA-A2/K(b)-transgenic mice," Int. J. Cancer, Feb. 2001, 91(3):385-392.

(56)                References Cited

OTHER PUBLICATIONS

Imai et al., "Exogenous antigens are processed through the endoplasmic reticulum-associated degradation (ERAD) in cross-presentation by dendritic cells," Int. Immunology, Jan. 2005, 17(1):45-53.

Jackson et al., "A totally synthetic vaccine of generic structure that targets Toll-like receptor 2 on dendritic cells and promotes antibody or cytotoxic T cell responses" Proc. Natl. Acad. Sci. U.S.A., Oct. 2004, 101(43):15440-15445.

Kaech et al., "Selective expression of the interleukin 7 receptor identifies effector CD8 T cells that give rise to long-lived memory cells," Nat. Immunology, Dec. 2003, 4(12):1191-1198.

Karosiene et al., "NetMHCIIpan-3.0, a common pan-specific MHC class II prediction method including all three human MHC class II isotypes, HLA-DR, HLA-DP and HLA-DQ," Immunogenetics, Oct. 2013, 65(10):711-724.

Karyampudi et al., "A degenerate HLA-DR epitope pool of HER-2/neu reveals a novel in vivo immunodominant epitope, HER-2/neu88-102," Clin. Cancer Research, Feb. 1, 2010, 16(3):825-834.

Katz et al., "T cell receptor stimulation impairs IL-7 receptor signaling by inducing expression of the microRNA miR-17 to target Janus kinase 1," Sci. Signaling, Aug. 26, 2014, 7(340):ra83, 10 pages.

Kisselev et al., "Proteasome inhibitors: from research tools to drug candidates," Chem. Biology, Aug. 2001, 8(8):739-758.

Knutson et al., "IL-12 enhances the generation of tumour antigen-specific Th1 CD4 T cells during ex vivo expansion," Clin. Exp. Immunology, Feb. 2004, 135(2):322-329.

Knutson et al., "Immunization with a HER-2/neu helper peptide vaccine generates HER-2/neu CD8 T-cell immunity in cancer patients," J. Clin. Investigation, Feb. 2001, 107(4):477-484.

Kobayashi et al., "Defining promiscuous MHC class II helper T-cell epitopes for the HER2/neu tumor antigen," Cancer Research, Sep. 15, 2000, 60(18):5228-5236.

Koenen et al., "Mutually exclusive regulation of T cell survival by IL-7R and antigen receptor-induced signals," Nat. Communications, Apr. 16, 2013, 4:1735, 10 pages.

Kovjazin et al., "ImMucin: a novel therapeutic vaccine with promiscuous MHC binding for the treatment of MUC1-expressing tumors," Vaccine, Jun. 24, 2011, 29(29-30):4676-4686.

Kreer et al., "Cross-presentation: how to get there—or how to get the Erm" Front. Immunology, Jan. 3, 2012, 2:87, 10 pages.

Kruit et al., "Selection of immunostimulant AS15 for active immunization with MAGE-A3 protein: results of a randomized phase II study of the European Organisation for Research and Treatment of Cancer Melanoma Group in Metastatic Melanoma," J. Clin. Oncology, Jul. 1, 2013, 31(19):2413-2420.

Lu et al., "Efficient identification of mutated cancer antigens recognized by T cells associated with durable tumor regressions," Clin. Cancer Research, Jul. 1, 2014, 20(13):3401-3410.

Madan et al., "Clinical evaluation of TRICOM vector therapeutic cancer vaccines," Semin. Oncology, Jun. 2012, 39(3):296-304.

Markley et al., "IL-7 and IL-21 are superior to IL-2 and IL-15 in promoting human T cell-mediated rejection of systemic lymphoma in immunodeficient mice," Blood, Apr. 29, 2010, 115(17):3508-3519.

McKinstry et al., "Effector CD4 T-cell transition to memory requires late cognate interactions that induce autocrine IL-2," Nat. Communications, Nov. 5, 2014, 5:5377, 12 pages.

Melief et al., "Immunotherapy of established (pre)malignant disease by synthetic long peptide vaccines," Nat. Rev. Cancer, May 2008, 8(5):351-360.

Men et al., "MHC class I- and class II-restricted processing and presentation of microencapsulated antigens," Vaccine, Mar. 5, 1999, 17(9-10):1047-1056.

Ménager et al., "Cross-presentation of synthetic long peptides by human dendritic cells: a process dependent on ERAD component p97/VCP but Not sec61 and/or Derlin-1," PLoS One, Feb. 27, 2014, 9(2):e89897, 13 pages.

Morgan et al., "High efficiency TCR gene transfer into primary human lymphocytes affords avid recognition of melanoma tumor antigen glycoprotein 100 and does not alter the recognition of autologous melanoma antigens," J. Immunology, Sep. 15, 2003, 171(6):3287-3295.

Nielsen et al., "NetMHCIIpan-2.0—Improved pan-specific HLA-DR predictions using a novel concurrent alignment and weight optimization training procedure," Immunome Res., Nov. 2010, 6:9.

PCT International Preliminary Report on Patentability in International Appln. No. PCT/US2016/064749, dated Jun. 5, 2018, 8 pages.

PCT International Search Report and Written Opinion in International Appln. No. PCT/US2016/064749, dated Apr. 28, 2017, 13 pages.

Peng et al., "Helper-independent, L-selectin(low) CD8(+) T cells with broad anti- tumor efficacy are naturally sensitized during tumor progression," J. Immunology, Nov. 15, 2000, 165(10):5738-5749.

Quoix et al., "Therapeutic vaccination with TG4010 and first-line chemotherapy in advanced non-small-cell lung cancer: a controlled phase 2B trial," Lancet Oncology, Nov. 2011, 12(12):1125-1133.

Rongcun et al., "Identification of new HER2/neu-derived peptide epitopes that can elicit specific CTL against autologous and allogeneic carcinomas and melanomas," J. Immunology, Jul. 15, 1999, 163(2):1037-1044.

Rosalia et al., "Dendritic cells process synthetic long peptides better than whole protein, improving antigen presentation and T-cell activation," Eur. J. Immunology, Oct. 2013, 43(10):2554-2565.

Sabbatini et al., "Phase I trial of overlapping long peptides from a tumor self-antigen and poly-ICLC shows rapid induction of integrated immune response in ovarian cancer patients," Clin. Cancer Research, Dec. 1, 2012, 18(23):6497-6508.

Salazar et al., "Persistent immunity and survival after immunization with a HER2/neu (HER2) vaccine," J. Clin. Oncology, May 20, 2009, 27(15_suppl):3010, 4 pages.

Sinnathamby et al., "Presentation by recycling MHC class II molecules of an influenza hemagglutinin-derived epitope that is revealed in the early endosome by acidification," J. Immunology, Apr. 1, 2003, 170(7):3504-3513.

Slingluff Jr. et al., "A randomized phase II trial of multiepitope vaccination with melanoma peptides for cytotoxic T cells and helper T cells for patients with metastatic melanoma (E1602)," Clin. Cancer Research, Aug. 1, 2013, 19(15):4228-4238.

Slingluff Jr. et al., "Immunologic and clinical outcomes of a randomized phase II trial of two multipeptide vaccines for melanoma in the adjuvant setting," Clin. Cancer Research, Nov. 1, 2007, 13(21):6386-6395.

Surman et al., "Localization of CD41 T cell epitope hotspots to exposed strands of HIV envelope glycoprotein suggests structural influences on antigen processing," Proc. Natl. Acad. Sci. USA, Apr. 10, 2011, 98(8):4587-4592.

Tewari et al., "A cytosolic pathway for MHC class II-restricted antigen processing that is proteasome and TAP dependent," Nat. Immunology, Mar. 2005, 6(3):287-294.

Tran et al., "Cancer immunotherapy based on mutation-specific CD4+ T cells in a patient with epithelial cancer," Science, May 9, 2014, 344(6184):641-645.

Wang et al., "Adoptive transfer of tumor-primed, in vitro-activated, CD4(+) T effector cells (T(E)s) combined with CD8(+) T(E)s provides intratumoral T-E proliferation and synergistic antitumor response," Blood, Jun. 1, 2007, 109(11):4865-4872.

Wang et al., "CMVpp65 Vaccine Enhances the Antitumor Efficacy of Adoptively Transferred CD19-Redirected CMV-Specific T Cells," Clin. Cancer Res., Jul. 2015, 21(13):2993-3002.

Zehner et al., "The translocon protein sec61 mediates antigen transport from endosomes into the cytosol for cross-presentation to CD8(+) T cells," Immunity, May 19, 2015, 42(5):850-863.

Zeng et al., "Synergy of IL-21 and IL-15 in regulating CD8+ T cell expansion and function," J. Exp. Medicine, Jan. 3, 2005, 201(1):139-148.

Zhang et al., "Comparing pooled peptides with intact protein for accessing cross-presentation pathways for protective CD8+ and CD4+ T cells," J. Biol. Chemistry, Apr. 3, 2009, 284(14):9184-9191.

(56) References Cited

OTHER PUBLICATIONS

Zhang et al., "Hotspot Hunter: a computational system for large-scale screening and selection of candidate immunological hotspots in pathogen proteomes," BMC Bioinformatics, 2008, 9(Suppl 1):S19, 9 pages.

* cited by examiner

FIG. 1

(SEQ ID NO:76)

FIG. 2A
MUC1
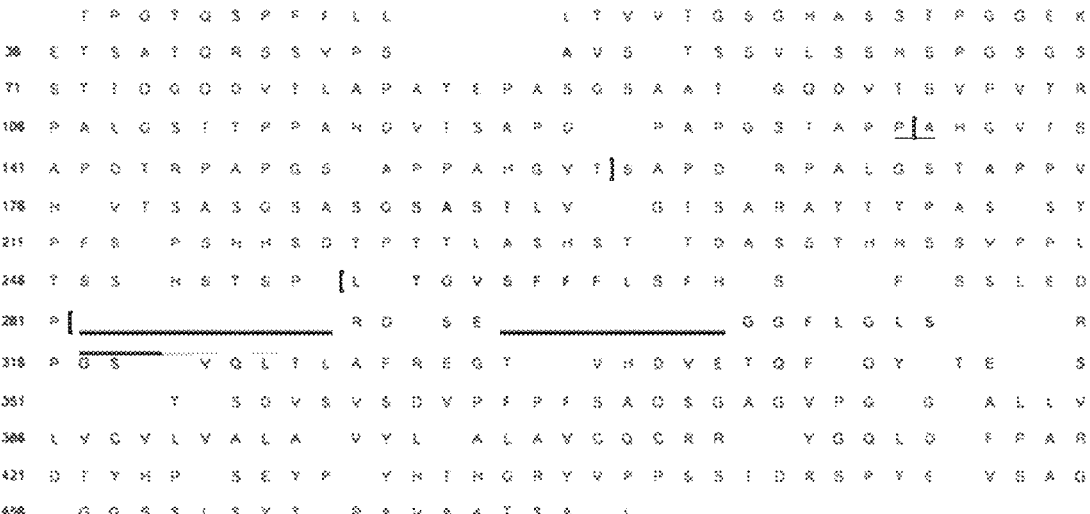
FIG. 2B
HER2/neu
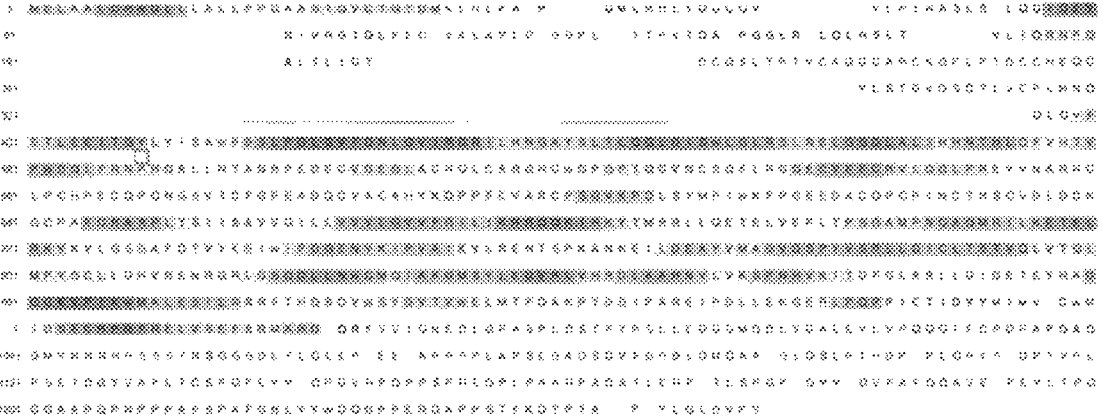
FIG. 2C
modified CALR C-terminus

1

METHODS AND VACCINES FOR INDUCING IMMUNE RESPONSES TO MULTIPLE DIFFERENT MHC MOLECULES

CROSS-REFERENCE TO RELATED APPLICATIONS

This application is a continuation of U.S. application Ser. No. 15/781,393, filed Jun. 4, 2018, which is a National Stage Application under 35 U.S.C. § 371 that claims the benefit of Application Serial No. PCT/US2016/064749, filed Dec. 2, 2016, which also claims the benefit of U.S. Provisional Application Ser. No. 62/263,256, filed Dec. 4, 2015. The disclosures of the prior applications are considered part of (and are incorporated by reference in) the disclosure of this application.

STATEMENT AS TO FEDERALLY SPONSORED RESEARCH

This invention was made with government support under CA136632 and CA102701 awarded by the National Institutes of Health. The federal government has certain rights in the invention.

SEQUENCE LISTING

This application contains a Sequence Listing that has been submitted electronically as an XML file named 07039-1505002sub_SL.xml. The XML file, created on Oct. 1, 2025, is 101,504 bytes in size. The material in the XML file is hereby incorporated by reference in its entirety.

1. BACKGROUND

1. Technical Field

This document provides methods and materials relating to isolated polypeptides, polypeptide preparations, vaccine preparations (e.g., anti-cancer vaccine preparations), and methods for vaccinating mammals. For example, this document provides polypeptides having the ability to be processed into a collection of different polypeptides such that the polypeptides of the collection are capable of being presented by different major histocompatibility complex (MHC) molecules present in a particular mammalian population.

2. Background Information

Polypeptide-based vaccines use polypeptide sequences derived from target proteins as epitopes to provoke an immune reaction. These vaccines are a result of an improved understanding of the molecular basis of epitope recognition, thereby permitting the development of rationally designed, epitope-specific vaccines based on motifs demonstrated to bind to MHC molecules.

SUMMARY

This document provides methods and materials relating to isolated polypeptides, polypeptide preparations, vaccine preparations (e.g., anti-cancer vaccine preparations), and methods for vaccinating mammals. For example, this document provides polypeptides (e.g., CMV pp65, MUC1, HER2, Mesothelin (MESO), TRAG-3, or Calreticulin (CALR) polypeptides) having the ability to be processed into different polypeptides such that the processed polypeptides as a group are capable of being presented by different MHC molecules present in a particular mammalian population. In some cases, the group of processed polypeptides can bind to at least 85 percent (e.g., at least about 87, 90, of 95 percent) of the MHC molecules present in a particular mammalian population such as humans.

This document also provides methods and materials (e.g., vaccine preparations) for treating cancer. For example, the vaccine preparations provided herein can include one or more of the MUC1, HER2, MESO, TRAG-3, or CALR polypeptides provided herein (see, e.g., Table 1) and can have the ability to induce a protective or therapeutic immune response within a mammal (e.g., a human).

As described herein, polypeptides ranging from about 18 to about 55 (e.g., about 18 to about 50, about 20 to about 50, about 25 to about 50, about 30 to about 50, about 18 to about 45, about 18 to about 40, about 18 to about 35, about 20 to about 45, about 25 to about 40, or about 30 to about 35) amino acid residues in length were identified, produced, and confirmed to have the ability to induce immune responses in the context of multiple different MHC molecules. The identification of these polypeptides can be used to aid in understanding immune processes and can be used to generate anti-cancer vaccine preparations.

In general, one aspect of this document features an isolated polypeptide, wherein the amino acid sequence of the polypeptide is as set forth in any one of SEQ ID NOs:1-58.

In another aspect, this document features a composition comprising, or consisting essentially of, at least one isolated polypeptide selected from the group consisting of SEQ ID NOs:1-58. The composition can further comprise an adjuvant.

In another aspect, this document features a method of treating cancer or a precancerous condition in a mammal. The method comprises, or consists essentially of, administering to the mammal a composition comprising an adjuvant and at least one polypeptide, wherein the amino acid sequence of the polypeptide is as set forth in any one of SEQ ID NOs:1-58. The mammal can be a human. The cancer can be breast cancer, pancreatic cancer, ovarian cancer, stomach cancer, lung cancer, colon cancer, multiple myeloma, leukemia, brain cancer, or melanoma cancer. The precancerous condition can be primary myelofibrosis, essential thrombocythemia or polycythemia vera. The adjuvant can be CpG, aluminum sulfate, aluminum phosphate, MF59, Pam3CSK4, LPS, polyIC, imiquimod, or R848.

In another aspect, this document features a vaccine comprising an adjuvant and at least one polypeptide, wherein the amino acid sequence of the polypeptide is as set forth in any one of SEQ ID NOs:1-58. The adjuvant can be CpG, aluminum sulfate, aluminum phosphate, MF59, Pam3CSK4, LPS, polyIC, imiquimod, or R848.

In another aspect, this document features a method of inducing an immune response against at least one polypeptide, wherein the sequence of the polypeptide is as set forth in any one of SEQ ID NOs:1-58, wherein the method comprises administering the polypeptide to a mammal in an amount effective to induce an immune response against the polypeptide. The polypeptide can be administered in combination with an adjuvant. The adjuvant can be CpG, aluminum sulfate, aluminum phosphate, MF59, Pam3CSK4, LPS, polyIC, imiquimod, or R848.

In another aspect, this document features a method of identifying a polypeptide between 18 and 50 amino acids in length, wherein the polypeptide includes epitopes that bind to at least 20 different HLA-DR types, wherein the method comprises determining the binding affinity of epitopes within the polypeptide for the at least 20 different HLA-DR types. The at least 20 different HLA-DR types can be selected by identifying (a) HLA-DRB1 alleles with greater than 6% frequency in 1 or more population groups, (b) HLA-DRB1 alleles with greater than 3% frequency in 2 or more population groups, (c) HLA-DRB1 alleles with greater than 1.5% frequency in 3 or more population groups, and (d) for population groups with less than 89.0% coverage, adding the next highest allele frequencies for that group, until 89% coverage.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 illustrates promising MHC binding peptide epitopes identified using the program "SYFPEITHI." The illustration analyzes the full the amino acid sequence for the protein MUC1 (SEQ ID NO:76). The part of the sequence located inside the box represents the variable number of tandem repeats domain (VNTR). Each sequence underlined and labeled with "#" is predicted to bind to the limited number (six) of HLA-DR molecules that are included in the SYFPEITHI algorithm. Each sequence underlined and labeled with "##" is predicted to bind to HLA-A2, as predicted by the SYFPEITHI algorithm. Areas labeled with "A" have both HLA-DR and HLA-A2 predicted epitopes. The numbers beside represent SYFPEITHI arbitrary binding scores+/−standard deviation for the HLA-DR types tested by SYFPEITHI. This type of analysis has been employed to synthesize peptides 15-17 amino acids long which can directly bind to HLA-DRB1 (MHC Class II) molecules, as well as peptides 8-9 amino acids long which can directly bind to HLA-A2 (MHC Class I) molecules.

FIGS. 2A-2C are results from an antigen discovery algorithm. FIG. 2A is the amino acid sequence for a MUC1 polypeptide (SEQ ID NO:77). Each amino acid is shaded based upon the frequency of HLA-DRB1 (MHC Class II) molecules that epitope is predicted to bind. Epitopes begin with the shaded-coded amino acid and are 15 amino acids long. "Dead" epitopes are light in shade and range to darker for epitopes with a high frequency of binding. This allows for a graphical "heat map" of the immunogenic regions within polypeptides and graphically represents the advancement over other techniques for the polypeptides described herein. FIG. 2B is a similarly derived "heat map" of a human HER2 polypeptide (SEQ ID NO:78) with a similar scale to graphically represent "hot spots" of epitopes displaying affinity for multiple MHC Class II molecules. FIG. 2C is a heat map of a 40 aa C-terminal neo-epitope of a human calreticulin (CALR) polypeptide (SEQ ID NO:79).

DETAILED DESCRIPTION

Figure 3:
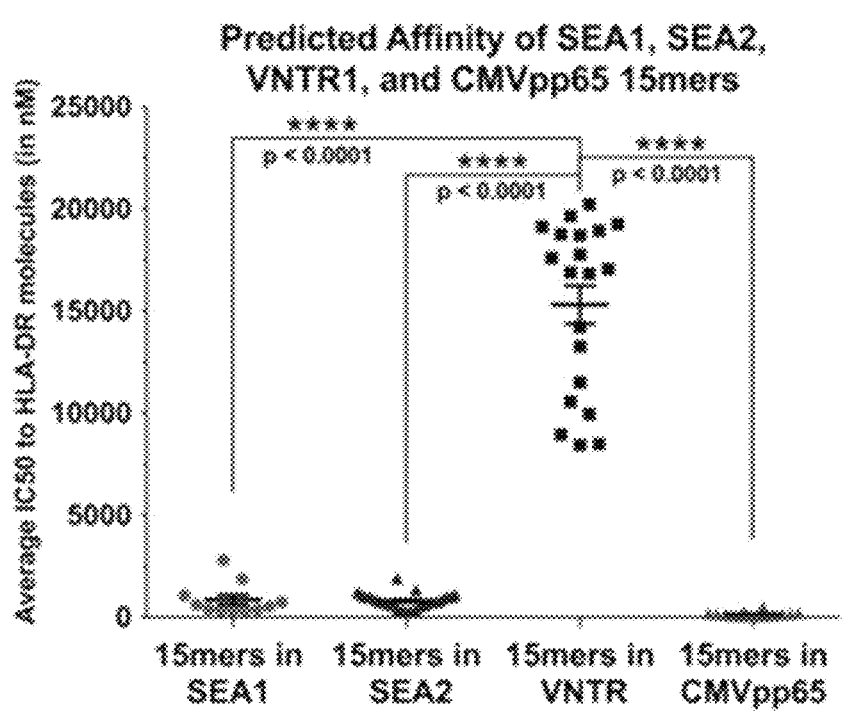
FIG. 3 is a graph plotting the average predicted affinities ($IC_{50}$) for cleavable 15-mer epitopes within SEA1, SEA2, VNTR1, and CMV pp65 polypeptides.

This document provides isolated polypeptides, polypeptide preparations, vaccine preparations (e.g., anti-cancer vaccine preparations), and methods for vaccinating mammals. For example, this document provides polypeptides that have the ability to be naturally processed and presented by different MHC molecules. In some cases, a polypeptide provided herein can have a sequence present in a cancer antigen polypeptide such as a MUC1, HER2, MESO, TRAG-3, or CALR polypeptide.

In general, a polypeptide provided herein is a fragment of a full-length polypeptide that is longer than 18 amino acid residues in length and shorter than the full length polypeptide. For example, a polypeptide provided herein can range from about 18 to about 55 (e.g., about 18 to about 50, about 20 to about 50, about 25 to about 50, about 30 to about 50, about 18 to about 45, about 18 to about 40, about 18 to about 35, about 20 to about 45, about 25 to about 40, or about 30 to about 35) amino acid residues in length. In some cases, a polypeptide provided herein can have the ability to induce immune responses in the context of multiple different MHC molecules. Examples of polypeptides provided herein include, without limitation, the polypeptides set forth in SEQ ID NOs:1-58 (Table 1).

TABLE 1

Examples of immunogenic polypeptides.

| SEQ ID NO: | Testing/ Details | Amino acid sequence (length) |
|---|---|---|
| 1 | */CMV pp65 | SQEPMSIYVYALPLKMLNIPSINVHHYP (28 aa) |
| 2 | MUC1 (N-terminus domain) | VPSSTEKNAVSMTSSVLSSHSPGSGSSTTQGQ (32 aa) |
| 3 | */MUC1 (degenerate repeat domain) | NRPALGSTAPPVHNVTSASGSASGSASTLV (30 aa) |
| 4 | MUC1 (degenerate repeat domain) | STAPPVHNVTSASGSASGSASTLVHNGTSARATTTPA (37 aa) |
| 5 | */MUC1 (SEA1 domain) | STSPQLSTGVSFFFLSFHISNLQFNSSLEDPSTD (34 aa) |
| 6 | */MUC1 (SEA2 domain) | STDYYQELQRDISEMFLQIYKQGGFLGLSNIKFRPGSVV (39 aa) |
| 7 | */MUC1 (SEA3 domain) | VHDVETQFNQYKTEAASRYNLTISDVSVSDVPFP (34 aa) |
| 8 | HER2 | MELAALCRWGLLLALLPPGAASTQVCT (27 aa) |
| 9 | HER2 | PASPETHLDMLRHLYQGCQVVQGNLELT (28 aa) |
| 10 | HER2 | VVQGNLELTYLPTNASLSFLQDIQEV (26 aa) |
| 11 | ¶/HER2 | LSFLQDIQEVQGYVLIAHNQVRQVPLQRL (29 aa) |
| 12 | ¶/HER2 | AHNQVRQVPLQRLRIVRGTQLFEDNYALA (29 aa) |
| 13 | ¶/HER2 | TEILKGGVLIQRNPQLCYQDTILWKDIFH (29 aa) |
| 14 | ¶/HER2 | YQDTILWKDIFHKNNQLALTLIDTNRSRACHPC (33 aa) |
| 15 | HER2 | LGMEHLREVRAVTSANIQEFAGC (23 aa) |
| 16 | ¶/HER2 | NIQEFAGCKKIFGSLAFLPESFDGDP (26 aa) |
| 17 | ¶/HER2 | VFETLEEITGYLYISAWPDSLPDLSV (26 aa) |
| 18 | ¶/HER2 | DLSVFQNLQVIRGRILHNGAYSLTLQGLG (29 aa) |
| 19 | HER2 | TLQGLGISWLGLRSLRELGSGLALIHHN (28 aa) |
| 20 | ¶/HER2 | ELGSGLALIHHNTHLCFVHTVPW (23 aa) |

TABLE 1-continued

Examples of immunogenic polypeptides.

| SEQ ID NO: | Testing/ Details | Amino acid sequence (length) |
|---|---|---|
| 21 | HER2 | HNTHLCFVHTVPWDQLFRNPH (21 aa) |
| 22 | HER2 | PSGVKPDLSYMPIWKFPDEEG (21 aa) |
| 23 | HER2 | EQRASPLTSIISAVVGILLVVV (22 aa) |
| 24 | ¶/HER2 | IKRRQQKIRKYTMRRLLQETELVEPLTPS (29 aa) |
| 25 | HER2 | QAQMRILKETELRKVKVLGSGAFGTVYK (28 aa) |
| 26 | ¶/HER2 | GVGSPYVSRLLGICLTSTVQLVTQLM (26 aa) |
| 27 | HER2 | DLLNWCMQIAKGMSYLEDVRL (21 aa) |
| 28 | HER2 | LEDVRLVHRDLAARNVLVKSP (21 aa) |
| 29 | ¶/HER2 | DLAARNVLVKSPNHVKITDFG (21 aa) |
| 30 | ¶/HER2 | DGGKVPIKWMALESILRRRFTHQS (24 aa) |
| 31 | HER2 | ESILRRRFTHQSDVWSYGV (19 aa) |
| 32 | HER2 | RLPQPPICTIDVYMIMVKCWMIDSECR (27 aa) |
| 33 | ¶/HER2 | SECRPRFRELVSEFSRMARDPQRFVVIQ (28 aa) |
| 34 | HER2 | ARDPQRFVVIQNEDLGPASP (20 aa) |
| 35 | MESO | ALGSLLFLLFSLGWVQPSRTLAGETGQ (27 aa) |
| 36 | MESO | GLSTERVRELAVALAQKNVKLSTEQLR (27 aa) |
| 37 | MESO | LDALPLDLLLFLNPDAFSGPQAC (23 aa) |
| 38 | MESO | FLNPDAFSGPQACTRFFSRITKANVDLLPRGAP (33 aa) |
| 39 | MESO | PSTWSVSTMDALRGLLPVLGQPIIRSIPQGIVAAWRQRSSRDPS (44 aa) |
| 40 | MESO | PSTWSVSTMDALRGLLPVLGQPIIRSIPQG (30 aa) |
| 41 | MESO | ALRGLLPVLGQPIIRSIPQGIVAAWRQRSSRDPS (34 aa) |
| 42 | MESO | PSTWSVSTMDALRGLLPVLGQPIIRSIPQGIVAAWRQRSSRDPS (44 aa) |
| 43 | MESO | QGYPESVIQHLGYLFLKMSPEDIRKWNVT (29 aa) |
| 44 | MESO | PEDIRKWNVTSLETLKALLEVNKGH (25 aa) |
| 45 | MESO | NMNGSEYFVKIQSFLGGAPTED (22 aa) |
| 46 | MESO | SQQNVSMDLATFMKLRTDAVLPLTVAEV (28 aa) |
| 47 | MESO | SQQNVSMDLATFMKLRTDAVLPLTVAE (27 aa) |
| 48 | MESO | DAVLPLTVAEVQKLLGPHVEGLKAE (25 aa) |
| 49 | MESO | GGIPNGYLVLDLSMQEALSGTPCLLGPGPV (30 aa) |
| 50 | TRAG-3 | MWMGLIQLVEGVKRKDQGFLE (21 aa) |
| 51 | TRAG-3 | GFLEKEFYHKTNIKMRCEFLACWPAFTVLGEA (32 aa) |
| 52 | TRAG-3 | DQVDWSRLLRDAGLVKMSRKPRASSPLSN (29 aa) |
| 53 | CALR neo-epitope | RRMMRTKMRMRRMRRTRRKMSPARPRTSCREACLQGWTEA (40 aa) |
| 54 | CALR neo-epitope | RRMMRTKMRMRRMRRTRRKMSPAR (24 aa) |
| 55 | CALR neo-epitope | RRMMRTKMRMRRMRRTRR (18 aa) |

TABLE 1-continued

```
                     Examples of immunogenic polypeptides.

SEQ
ID      Testing/
NO:     Details          Amino acid sequence (length)

56      */MUC1           SPQLSTGVSFFFLSFHISNLQFNSSLEDPSTD (32 aa)
        (SEA1
        domain)

57      ¶/HER2           GVGSPYVSRLLGICLTSTVQLV (22 aa)

58      MUC1-VNTR        AHGVTSAPDTRPAPGSTAPPAHGV (24 aa)
```

*Represents polypeptides confirmed to be immunogenic in 4/4 healthy donors.
¶Represents polypeptides confirmed to be immunogenic in one healthy donor.

The term "isolated" refers to material which is substantially or essentially free from components which normally accompany the material as it is found in its native state. Thus, isolated polypeptides as described in this document do not contain at least some of the materials normally associated with the polypeptides in their in situ environment. The term "polypeptide" refers to a chain of amino acids linked by polypeptide bonds.

Any appropriate method can be used to obtain a polypeptide provided herein. For example, polypeptides having the sequence set forth in any one of SEQ ID NOs:1-58 can be obtained using polypeptide synthesizing methods. In some cases, a polynucleotide sequence encoding a polypeptide provided herein can be inserted into a plasmid or other vector that can then be delivered to hosts that can be induced to transcribe and translate the polynucleotide into the polypeptide. In some cases, a polynucleotide sequence for a larger polypeptide can be inserted into host cells that can produce the larger polypeptide and then process that polypeptide into a smaller polypeptide or a functional variant of interest.

This document also provides compositions (e.g., anti-cancer vaccine compositions) containing one or more polypeptides provided herein. In some cases, a polypeptide provided herein can have the ability to be processed and presented by an MHC molecule. In some cases, the polypeptides set forth in SEQ ID NOs:1-58 can be used individually or as a mixture of two or more polypeptides to produce a composition (e.g., anti-cancer vaccine compositions). Any appropriate combination of the polypeptides listed in Table 1 can be used to produce a composition (e.g., anti-cancer vaccine compositions). For example, the combination can include at least 2, 3, 4, 5, 6, 7, 8, 9, 10, 11, 12, 13, 14, 15, 16, 17, 18, or more polypeptides selected from Table 1. For example, the polypeptides corresponding to SEQ ID NOs:2-7 can be used in any combination to produce an anti-cancer vaccine composition. In some cases, the polypeptides corresponding to SEQ ID NOs:2-7 and SEQ ID NOs:35-49 can be used in any combination to produce an anti-cancer vaccine composition. In some cases, a polypeptide having the amino acid sequence set forth in SEQ ID NO:2 and a polypeptide having the amino acid sequence set forth in SEQ ID NO:4 can be used together in any combination with one or more polypeptides of SEQ ID NOs:8-34 to produce an anti-cancer vaccine composition.

In some cases, a polypeptide provided herein (e.g., a polypeptide presented in Table 1) can include oxidized amino acid residues (e.g., oxidized forms of methionine) or can lack oxidized amino acid residues.

In some cases, a polypeptide provided herein (e.g., a polypeptide presented in Table 1) can include one or more modifications (e.g., post-translational modifications). Examples of post-translational modifications that can be present on a polypeptide provided herein include, without limitation, amidation (e.g., C-terminal amidation), acetylation (e.g., N-terminal acetylation), glycosylation, phosphorylation, and lipidation. For example, any one of SEQ ID NOs:1-58 can be amidated at the C-terminus and/or acetylated at the N-terminus. In cases where a mixture of two or more polypeptides provided herein are used, each polypeptide can be independently modified. For example, a combination of two or more of SEQ ID NOs:1-58 can include unmodified polypeptides, polypeptides amidated at the C-terminus, polypeptides acetylated at the N-terminus, and/or polypeptides amidated at the C-terminus and acetylated at the N-terminus.

A composition provided herein containing one or more polypeptides set forth in SEQ ID NOs:1-58 or any appropriate combination of polypeptides as described herein can be formulated to provide a polypeptide-based, anti-cancer vaccine. Any appropriate method can be used to formulate a polypeptide-based vaccine including, for example, those methods used to formulate polypeptide-based vaccines directed against other targets. Examples of polypeptide-based vaccines directed to other targets are described elsewhere (see, e.g., Belyakov et al., *Proc. Natl. Acad. Sci. U.S.A.*, 95 (4): 1709-1714 (1998) and Jackson et al., *Proc. Natl. Acad. Sci. U.S.A.*, 101 (43): 15440-15445 (2004)).

In some cases, a composition provided herein can be designed to treat cancer or a precancerous condition. For example, a composition (e.g., a vaccine composition) provided herein can have the ability to induce a therapeutic immune response against cancer cells within a mammal (e.g., a human). For example, a composition provided herein can have the ability to activate and, optionally, expand T-cells obtained from a mammal (e.g., a human) in culture.

A polypeptide provided herein (e.g., a polypeptide set forth in Table 1) can be formulated into a vaccine composition using any appropriate method. In some cases, a polypeptide provided herein can be combined with a pharmaceutically acceptable carrier or pharmaceutical excipient. The term "pharmaceutically acceptable" refers to a generally non-toxic, inert, and/or physiologically compatible composition. A term "pharmaceutical excipient" includes materials such as adjuvants, carriers, pH-adjusting and buffering agents, tonicity adjusting agents, wetting agents, preservatives, and the like. Examples of adjuvants include, without limitation, CpG, aluminum sulfate, aluminumphosphylate, MF59, Pam3CSK4, LPS, polyIC, imiquimod, and R848. In some cases, vaccines or components of a vaccine can be conjugated to, for example, a polysaccharide or other molecule, to improve stability or immunogenicity of one or more vaccine components. In some cases, a polypeptide provided herein (e.g., a polypeptide set forth in Table 1) can be formulated into a vaccine composition containing cells. For example, one or more polypeptides provided herein can be included within a cellular vaccine. Any appropriate method can be used to prepare a cellular vaccine or the components of a cellular vaccine.

This document also provides methods and materials (e.g., vaccines) for treating cancer or a precancerous condition. For example, the vaccines provided herein can include one or more of the cancer antigen polypeptides provided herein and can have the ability to induce a therapeutic immune response against cancer cells within a mammal (e.g., a human). For example, the compositions provided herein can include one or more of the cancer antigen polypeptides provided herein and can have the ability to activate and, optionally, expand T-cells obtained from a mammal (e.g., a human) in culture. Activated T-cells can be used in an immunotherapy (e.g., adoptive T-cell therapy), and can be administered to a mammal (e.g., a human) to induce a therapeutic immune response against cancer cells within the mammal. Any appropriate type of cancer can be treated using the methods and materials provided herein. For example, breast cancer, pancreatic cancer, ovarian cancer, stomach cancer, lung cancer, colon cancer, multiple myeloma, leukemia, brain cancer, and melanoma cancer can be treated using the methods and materials provided herein. Any appropriate type of precancerous condition can be treated using the methods and materials provided herein. For example, myelofibrosis (e.g., primary myelofibrosis), essential thrombocythemia, and polycythemia vera can be treated using the methods and materials provided herein.

In some cases, a composition provided herein (e.g., an anti-cancer vaccine composition) can be administered to a mammal having cancer or a precancerous condition under conditions effective to reduce the severity of one or more symptoms of the cancer or precancerous condition and/or to reduce the number of cancer cells or precancerous cells present within the mammal. Treatment of individuals having cancer or a precancerous condition can include the administration of a therapeutically effective amount of one or more polypeptides provided herein (e.g., one or more of SEQ ID NOs:1-58). In some cases, treatment can include the use of one or more polypeptides set forth in SEQ ID NOs:1-58 individually or as a mixture. The polypeptides can be used or administered as a mixture, for example, in equal amounts, or individually, provided in sequence, or administered all at once. The term "therapeutically effective amount" as used with treating cancer or a precancerous condition refers to that amount of the agent sufficient to reduce one or more symptoms of the cancer of precancerous condition and/or to reduce the number of cancer cells or precancerous cells within a mammal. In providing a subject with a polypeptide provided herein (e.g., an anti-cancer vaccine composition) capable of inducing a therapeutic effect, the amount of administered agent will vary depending upon such factors as the subject's age, weight, height, sex, general medical condition, previous medical history, etc. The subject can be, for example, a mammal. The mammal can be any type of mammal including, without limitation, a mouse, rat, dog, cat, horse, sheep, goat, cow, pig, monkey, or human.

The invention will be further described in the following examples, which do not limit the scope of the invention described in the claims.

EXAMPLES

Example 1—Identification of Long Polypeptides Having Promiscuous MHC Binding Capabilities There are two classes of MHC molecules: MHC Class I and Class II that are involved in presentation of epitopes to T-cells. CD8$^+$ T-cells recognize epitopes that are typically 8-12 amino acids long, on MHC Class I. CD4$^+$ T-cells recognize epitopes that are typically 15-20 amino acids long, on MHC Class II. In order for T-cells to recognize these epitopes, the epitopes have to remain bound to MHC molecules, meaning that the affinity of epitopes for MHC molecules limits which epitopes are part of an immune response.

Within MHC Class I, there are three gene loci, HLA-A, -B, and -C that determine the protein sequence for these MHC Class I molecules, and thus the epitopes that are part of an immune response. While there is genetic diversity in these loci, within the HLA-A locus specifically, nearly 50% of the population has the same gene, HLA-A2. One can identify epitopes that bind to HLA-A2 and use these peptides to therapeutically treat HLA-A2 positive cancer patients, either as part of a vaccine or in another modality.

The MHC Class II gene loci, HLA-DP, -DQ, and -DR are much more genetically diverse. Of these loci, HLA-DR is the most studied, and its role in the presentation of epitopes to CD4$^+$ T-cells is best understood. HLA-DP and -DQ may have more specific roles that are not well suited for all situations where epitopes are presented to CD4$^+$ T-cells. Within the DR locus, the significant genetic diversity is attributable to diversity of HLA-DRB1 genes. Furthermore, specific HLA-DRB1 genes are associated with additional HLA-DRB genes (HLA-DRB3,4,5), which further diversify the repertoire of MHC Class II molecules in the population.

The strategy employed by HLA-A2 epitope identification may not work for HLA-DR; epitopes should bind to multiple HLA-DR types in order to be used rationally to treat cancer patients.

Figure 1:
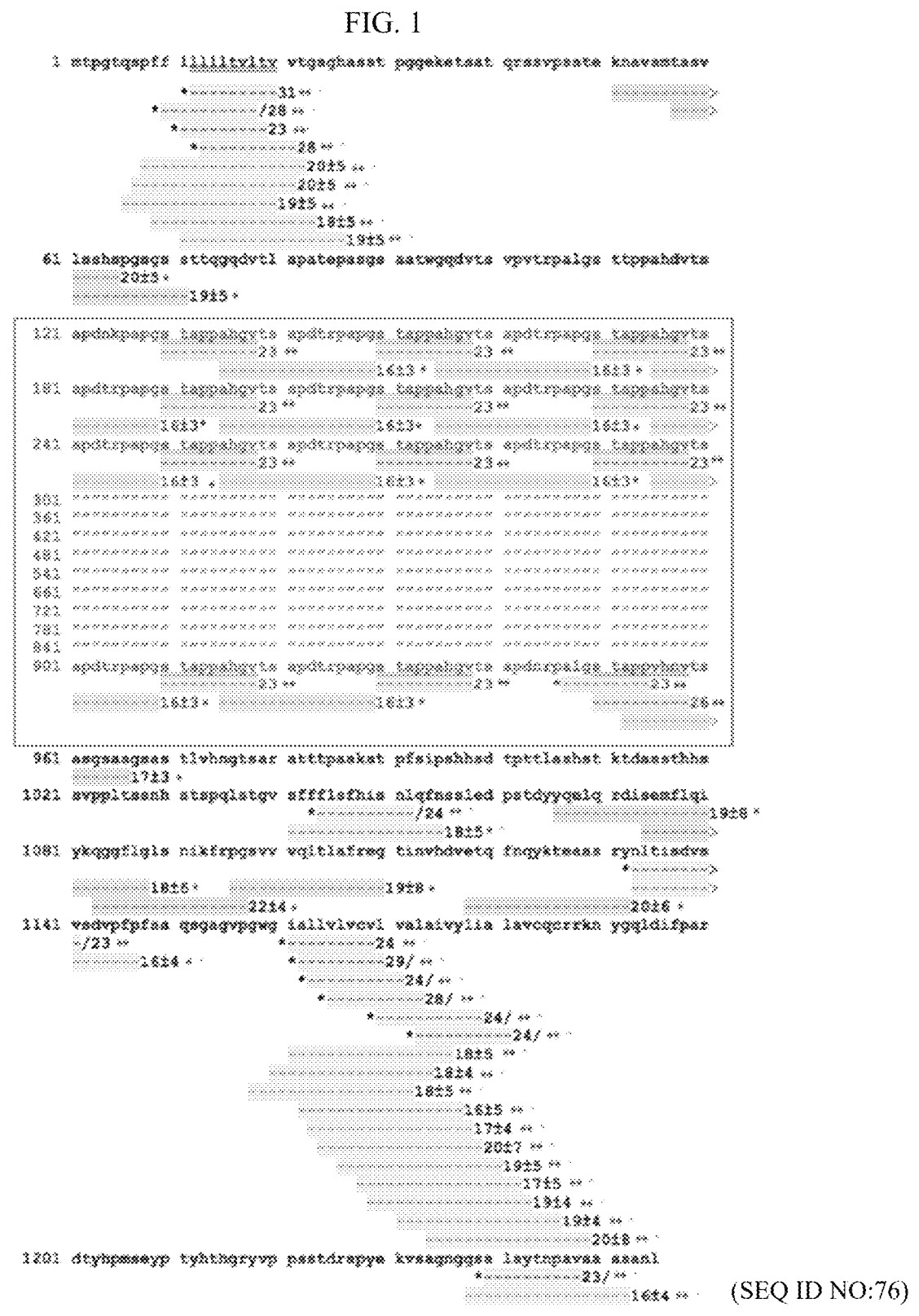

Initial investigations utilized a binding prediction algorithm SYFPEITHI, which scans only six HLA-DR types (HLA-DRB*0101, *0301, *0401, *0701, *1101 & *1501) and assigns arbitrary scores to epitopes based upon amino acids that are known to assist in the binding to MHC molecules. As an example, shown in FIG. 1, the entire sequence of the tumor associate antigen MUC1 was analyzed. Sequences underlined and labeled with ("#") were predicted to be binders to the HLA-DR types analyzed by SYFPEITHI. Scores shown are averages across the HLA-DR types+/−standard deviation. A few critical limitations of this method were identified:

1. The method predicted a large number of epitopes, which would limit throughput and the ability to rationally test all epitopes.
2. The method did not adequately delineate between epitopes in order to determine which should be stronger binders amongst the identified epitopes.
3. Most importantly, it did not encompass a wide enough cross section of HLA types to rationally treat enough patients.

Due to the large number HLA-DR types, it would be onerous to examine all of them to assess, which epitopes bind to the most HLA-DR types. The following was performed to rationally limit the investigation to HLA-DRB1, due to the fact that it is the most well studied HLA-DR molecule, epitope binding prediction algorithms were largely trained on HLA-DRB1 molecules, and the fact that HLA-DRB3, 4, and 5 only occur in conjunction with specific HLA-DRB1 genes.

Utilizing previously published data, the HLA-DRB1 diversity across multiple global ethnic groups resident within the United States was systematically examined. The goal was to ensure that nearly 9 in 10 patients across the seven main ethnic/racial groups would have HLA-DRB1 coverage. The following steps recapitulate the methodology:

1. HLA-DRB1 alleles with greater than 6% frequency in 1 or more population groups were chosen.
2. HLA-DRB1 alleles with greater than 3% frequency in 2 or more population groups were chosen.
3. HLA-DRB1 alleles with greater than 1.5% frequency in 3 or more population groups were chosen.
4. For population groups with less than 89.0% coverage, add next highest allele frequencies for that group, until 89% coverage.

As indicated in Table 2, 29 different HLA-DRB1 types were chosen that covered nearly 90% of each population, thus ensuring that nearly 9/10 people in the United States could respond. This level of population coverage was unattainable using other technologies.

likely to be bound to HLA-DRB1 molecules. Utilizing 500 nM or 750 nM as $IC_{50}$ binding cut offs, each full length cancer-associated polypeptide (MUC1, HER2, MESO, TRAG-3, and CALR) was scanned for binding to the 29 different HLA-DRB1 molecules.

This method allowed one to solve the first two problems by reducing the number of epitopes needed for study and allowing one to better rank and rationally evaluate the different epitopes. For example, compared to the SYF-PEITHI analysis, no HLA-DRB1 binding epitopes were identified within the variable number of tandem repeats (VNTR) domain of MUC1, a region that has been extensively studied. This increases throughput, reduces cost, and allows for more rational experimental designs.

Furthermore, the method provided additional granularity for determining epitopes that are more promiscuous or better binders than others. While almost all the epitopes were comparable to one another in the SYFPEITHI analysis, this new methodology clearly demonstrated that there are high value and low value epitopes within MUC1. An example of this is the SEA2 polypeptide, which contains the greatest density of extremely promiscuous epitopes, such that in the entire polypeptide there is at least one epitope that binds to

TABLE 2

Identification of HLA-DR Alleles Across Races and Ethnicities

| DRB1 Alleles | African American Frequency | Caucasian Frequency | Chinese Frequency | Hispanic Frequency | Indian Frequency | Japanese Frequency | Korean Frequency |
|---|---|---|---|---|---|---|---|
| 0101 | 2.65% | 8.60% | 0.93% | 4.33% | 3.21% | 5.84% | 5.78% |
| 0102 | 3.92% | 1.38% | 0.07% | 3.32% | 0.13% | 0.06% | 0.02% |
| 0301 | 6.99% | 12.16% | 6.81% | 6.95% | 7.46% | 0.66% | 2.20% |
| 0302 | 6.31% | 0.03% | 0.00% | 0.50% | 0.01% | 0.01% | 0.00% |
| 0401 | 2.02% | 8.78% | 0.51% | 1.81% | 0.90% | 1.15% | 0.78% |
| 0403 | 0.17% | 0.79% | 2.31% | 1.84% | 5.27% | 2.43% | 2.57% |
| 0404 | 0.82% | 3.88% | 0.88% | 5.78% | 2.01% | 0.32% | 1.39% |
| 0405 | 1.53% | 0.67% | 6.12% | 2.22% | 0.75% | 14.72% | 8.94% |
| 0407 | 0.39% | 1.12% | 0.08% | 7.47% | 0.13% | 0.64% | 0.44% |
| 0701 | 10.11% | 13.42% | 5.31% | 9.61% | 16.95% | 0.94% | 7.15% |
| 0802 | 0.09% | 0.08% | 0.55% | 9.64% | 0.51% | 4.34% | 2.50% |
| 0803 | 0.04% | 0.24% | 6.80% | 0.27% | 0.71% | 7.44% | 7.62% |
| 0804 | 5.42% | 0.20% | 0.01% | 0.88% | 0.08% | 0.02% | 0.00% |
| 0901 | 2.97% | 1.03% | 15.54% | 0.82% | 0.94% | 13.87% | 9.67% |
| 1001 | 1.92% | 0.85% | 1.34% | 1.30% | 6.28% | 0.40% | 1.70% |
| 1101 | 8.54% | 5.58% | 6.25% | 3.55% | 5.98% | 2.58% | 4.73% |
| 1104 | 0.58% | 2.95% | 0.25% | 3.25% | 1.97% | 0.12% | 0.07% |
| 1201 | 3.82% | 1.64% | 3.42% | 0.91% | 0.80% | 3.75% | 4.83% |
| 1202 | 0.29% | 0.02% | 11.50% | 0.15% | 2.99% | 1.71% | 3.45% |
| 1301 | 5.42% | 5.63% | 0.78% | 3.72% | 6.73% | 0.76% | 1.73% |
| 1302 | 7.30% | 4.88% | 2.42% | 3.50% | 3.37% | 5.75% | 8.62% |
| 1303 | 3.26% | 1.09% | 0.02% | 1.06% | 0.13% | 0.04% | 0.01% |
| 1401 | 1.86% | 2.61% | 3.33% | 1.84% | 1.13% | 3.01% | 2.68% |
| 1404 | 0.05% | 0.07% | 0.51% | 0.03% | 7.13% | 0.02% | 0.06% |
| 1406 | 0.01% | 0.02% | 0.02% | 4.27% | 0.05% | 1.42% | 0.68% |
| 1501 | 2.82% | 13.46% | 10.12% | 6.43% | 9.02% | 8.67% | 7.94% |
| 1502 | 0.23% | 0.72% | 2.88% | 1.17% | 10.73% | 9.67% | 3.18% |
| 1503 | 11.66% | 0.05% | 0.00% | 0.58% | 0.02% | 0.01% | 0.00% |
| 1602 | 1.38% | 0.15% | 4.35% | 2.47% | 0.67% | 0.67% | 0.99% |
| Total Coverage | 92.6% | 92.1% | 92.9% | 89.4% | 95.8% | 91.0% | 89.7% |

In order to examine this number of HLA-DRB1 molecules, different binding algorithm predictors were used. The netMHCII-pan-2.1 and -3.0 algorithms, which can make binding affinity predictions for the 29 HLA-DRB1 molecules under study (Nielsen et al., *Immunome Res.*, 6:9 (2010), and Karosiene et al., *Immunogenetics*, 65 (10): 711-724 (2013)) were chosen. Unlike SYFPEITHI, these predictors provided $IC_{50}$ binding affinities, allowing for a quantitative assessment of whether or not the 15-mers are all 29 HLA-DR molecules studied (Table 3). This level of prioritizing and being able to rationally rank targets is substantial compared to other methods.

In addition, the challenge of HLA-DR diversity in preventing the rational treatment of cancer patients was overcome. This is largely due to focusing on a greater number of HLA-DR molecules, but it was also due to the unexpected clustering of these promiscuous epitopes around one another within the polypeptide sequence. Many of these promiscuously binding epitopes within a polypeptide region were found to bind to a different set of HLA-DRB1 genes than the other epitopes within that region. This represents a lead break through, allowing for regions of polypeptides that are binders for 90% of the population, even if each epitope 5 within that region does not have the same degree of promiscuity.

Additionally, many of the polypeptides described herein, with 90% population coverage for MHC Class II, contained predicted HLA-A2 epitopes. This discovery allows for the rational targeting of both MHC Class I and Class II, with the potential to synthesize one or more long polypeptides (e.g., from 20 to 50 amino acid polypeptides) that encompass these epitopes and rationally treat cancer patients.

TABLE 3

| | | | |
|---|---|---|---|
| | | SEA2 | |
| | Embedded 15mers | Predicted Binding HLA-DRB1 Molecules | #Binders/Total |
| SEQ ID NO: 59 | DYYQELQRDISEMFL | 01.01, 01.02, 03.01, 03.02, 04.01, 04.05, 07.01, 08.03, 09.01, 10.01, 11.01, 11.04, 12.01, 12.02, 13.01, 13.02, 13.03, 14.06 | 18/29 |
| SEQ ID NO: 60 | YYQELQRDISEMFLQ | 01.01, 01.02, 03.01, 03.02, 04.01, 04.05, 07.01, 08.03, 09.01, 10.01, 11.01, 11.04, 12.01, 12.02, 13.01, 13.02, 13.03, 14.06 | 18/29 |
| SEQ ID NO: 61 | YQELQRDISEMFLQI | 01.01, 01.02, 03.01, 03.02, 04.01, 04.05, 07.01, 08.03, 09.01, 11.04, 12.01, 12.02, 13.01, 13.02, 13.03, 14.06 | 16/29 |
| SEQ ID NO: 62 | DISEMFLQIYKQGGF | 01.01, 01.02, 04.04, 04.05, 07.01, 08.03, 08.04, 10.01, 11.01, 11.04, 12.01, 12.02, 13.03, 14.04, 14.06, 15.01, 15.03, 16.02 | 18/29 |
| SEQ ID NO: 63 | ISEMFLQIYKQGGFL | 01.01, 01.02, 04.01, 04.04, 04.05, 07.01, 08.03, 08.04, 09.01, 10.01, 11.01, 11.04, 12.01, 12.02, 13.02, 13.03, 14.04, 14.06, 15.01, 15.02, 15.03, 16.02 | 22/29 |
| SEQ ID NO: 64 | SEMFLQIYKQGGFLG | 01.01, 01.02, 04.01, 04.04, 04.05, 07.01, 08.03, 08.04, 09.01, 10.01, 11.01, 11.04, 12.01, 12.02, 13.01, 13.03, 14.01, 14.04, 14.06, 15.01, 15.02, 15.03, 16.02 | 23/29 |
| SEQ ID NO: 65 | EMFLQIYKQGGFLGL | 01.01, 01.02, 04.01, 04.04, 04.05, 07.01, 08.03, 08.04, 09.01, 10.01, 11.01, 11.04, 12.01, 12.02, 13.01, 13.03, 14.01, 14.04, 14.06, 15.01, 15.02, 15.03, 16.02 | 23/29 |
| SEQ ID NO: 66 | MFLQIYKQGGFLGLS | 01.01, 01.02, 04.01, 04.04, 04.05, 07.01, 08.03, 08.04, 09.01, 10.01, 11.01, 11.04, 12.01, 12.02, 13.01, 13.03, 14.01, 14.04, 14.06, 15.01, 15.02, 15.03, 16.02 | 23/29 |
| SEQ ID NO: 67 | FLQIYKQGGFLGLSN | 01.01, 01.02, 07.01, 08.03, 08.04, 09.01, 10.01, 11.01, 11.04, 12.01, 12.02, 13.01, 13.03, 14.04, 14.06, 15.01, 15.02, 15.03, 16.02 | 19/29 |
| SEQ ID NO: 68 | LQIYKQGGFLGLSNI | 01.01, 01.02, 04.01, 04.05, 07.01, 08.03, 08.04, 09.01, 10.01, 11.01, 11.04, 12.01, 12.02, 13.01, 13.03, 14.06, 15.01, 15.03, 16.02 | 19/29 |
| SEQ ID NO: 69 | QIYKQGGFLGLSNIK | 01.01, 01.02, 04.01, 04.05, 08.03, 09.01, 10.01, 11.01, 11.04, 12.01, 12.02, 13.01, 13.03, 14.06, 15.01, 15.02, 15.03, 16.02 | 18/29 |
| SEQ ID NO: 70 | IYKQGGFLGLSNIKF | 01.01, 01.02, 04.01, 04.04, 04.05, 07.01, 08.03, 09.01, 10.01, 11.01, 11.04, 12.01, 12.02, 13.03, 14.04, 14.06, 15.01, 15.02, 15.03, 16.02 | 20/29 |

TABLE 3-continued

| | | Predicted Binding HLA-DRB1 | |
| | Embedded 15mers | Molecules | #Binders/Total |
| --- | --- | --- | --- |
| SEQ ID NO: 71 | YKQGGFLGLSNIKFR | 01.01, 01.02, 04.01, 04.04, 04.05,<br>04.07, 07.01, 08.03, 08.04, 09.01,<br>10.01, 11.01, 11.04, 12.01, 12.02,<br>13.01, 13.02, 13.03, 14.04, 14.06,<br>15.01, 15.02, 15.03, 16.02 | 24/29 |
| SEQ ID NO: 72 | KQGGFLGLSNIKFRP | 01.01, 01.02, 03.01, 04.01, 04.03,<br>04.04, 04.05, 04.07, 07.01, 08.03,<br>08.04, 09.01, 10.01, 11.01, 11.04,<br>12.01, 12.02, 13.03, 14.04, 14.06,<br>15.01, 15.02, 15.03, 16.02 | 24/29 |
| SEQ ID NO: 73 | QGGFLGLSNIKFRPG | 01.01, 01.02, 04.01, 04.04, 04.05,<br>04.07, 07.01, 08.03, 08.04, 09.01,<br>10.01, 11.01, 11.04, 12.01, 12.02,<br>13.03, 14.04, 14.06, 15.01, 15.02,<br>15.03, 16.02 | 21/29 |
| SEQ ID NO: 74 | GFLGLSNIKFRPGSV | 01.01, 01.02, 04.01, 04.04, 04.05,<br>07.01, 08.02, 08.03, 08.04, 09.01,<br>10.01, 11.01, 11.04, 12.01, 12.02,<br>13.01, 13.02, 13.03, 14.04, 14.06,<br>15.01, 15.02, 15.03, 16.02 01.01, | 24/29 |
| SEQ ID NO: 75 | FLGLSNIKFRPGSVV | 01.02, 04.01, 04.04, 07.01, 08.02,<br>08.03, 08.04, 09.01, 11.01, 11.04,<br>12.01, 12.02, 13.01, 13.02, 13.03,<br>14.04, 14.06, 15.01, 15.03, 16.02 | 21/29 |

The nature distribution of these clusters allowed for a graphical representation of the discovery, utilizing an intelligent "heat map" of activity. For each MHC Class II epitope (generally considered to be 15 amino acids long) within the entire polypeptide, a shading was assigned on a 29 shading gradient scale between light to dark depending on the number of HLA-DRB1 molecules that the epitope was predicted to bind to out of the 29 tested (using the predicted nM affinities). Epitopes with no predicted binding to any HLA-DRB1 molecules remained light, while a 29/29 was dark (e.g., "hot"). The amino acid at the N-terminus of the epitope bears the shade assigned for that epitope. This analysis allowed for a graphical representation of a polypeptide's immunologic "hot spots." The immunological hot spots for MUC1, HER2/neu, and a myelofibrosis-associated CALR C-terminal epitope are shown in FIGS. 2A, 2B, and 2C. The 40 aa C-terminus of CALR is a neo-epitope that is not present on CALR of healthy individuals, but is present on CALR in 80% of pre-leukemic patients.

For MUC1, the VNTR polypeptide (FIG. 2A, uppermost box) lacked hot spots in contrast to two hot polypeptides (next two boxes) designated as the SEA1 and SEA2 regions. For both MUC1 and HER2, the final 14 amino acids lacked hot spots because the sequences were too short to have a 15-mer epitope that begins with them. With this methodology, long polypeptides (e.g., longer than 20 amino acid residues) were successfully identified for several cancer-associated antigens (e.g., MUC1, HER2/neu, MESO, TRAG-3, and CALR) as containing a high density of promiscuous HLA-DR 15-mer epitopes.

To test the reliability of these results, the immune responses for MUC1 long polypeptides (SEA1 and SEA2) were compared to that generated using a pathogen polypeptide. To do this, the same identification methodology used for the tumor antigen polypeptides was used to identify hot spots in the cytomegalovirus (CMV) pp65 polypeptide. The hot spot sequence that was identified was used as a control as was the previously identified VNTR polypeptide. As shown in FIG. 3, the predicted average binding affinity across the 29 HLA-DRB1 genes for the 15-mer epitopes within the VNTR polypeptide was extremely high (in this case lower represents a lower amount of polypeptide needed to bind, and thus better), whereas the 15-mers embedded in the CMV long polypeptide, SEA1, and SEA2 were extremely low, thus meaning that the epitopes within CMV pp65, SEA1, and SEA2 are much tighter binders.

The SEA polypeptides, CMV long polypeptide, and VNTR polypeptide were tested in a culture system. Briefly, bulk peripheral blood mononuclear cells (PBMC) were thawed and exposed to GM-CSF on day 0 in culture. On day 1, cultures were exposed to the polypeptides (SEA1, SEA2, CMV pp65, or VNTR) and monocyte maturating agents (LPS and R848). On day 2, media was washed out, and the cells were split 1:6 in fresh media containing IL-7 for T-cell expansion. Further splits occurred with simple addition of more media containing IL-7 depending upon acidity of the media between days 7-15. On day 16, an antigen specific restimulation of T-cell cultures was performed utilizing fresh PBMC as the antigen presenting cells. These fresh PBMC were thawed on day 14 and treated the same way as the initial culture on days 0-1, before being used on day 16. At the time of restimulation, an intracellular cytokine assay was performed. The T-cell cultures also were allowed to proliferate for an additional 14 days in media containing IL-7. At the end of culture, day 28, T-cells were further tested with a new intracellular cytokine assay utilizing fresh PBMC, prepared the same way as the PBMC used on day 16 for the first intracellular cytokine assay. Representative dot-plots for IFNγ levels are shown for the CMV pp65 polypeptide and the SEA2 polypeptide, with levels being much lower when T-cells were not restimulated with the same polypeptide they saw at the initiation of culture. As shown in FIGS.

4C and D, in contrast to the VNTR polypeptide, the CMV long polypeptide, SEA1 long polypeptide, and SEA2 long polypeptide consistently exhibited an immune response by antigen specific IFNγ production. Each data point represents the level of IFNγ after subtracting the levels of IFNγ from restimulation with irrelevant polypeptides or no polypeptide from levels when T-cells were restimulated with the original polypeptide.

Other polypeptides as indicated in Table 1 were tested and confirmed to produce detectable immune responses.

Example 2—Expansion of CD4$^+$ and CD8$^+$ T-Cells with Enriched Specificity for Tumor-Associated Long Synthetic Polypeptides Whether GM+R848+LPS conditioned PBMC could process exogenous synthetic peptides as effectively as *Candida albicans* extract (CAN) extract or recombinantly produced HER2-ICD was examined.

The following long peptides were synthesized for immunotargeting:

```
CMVpp65-derived 28 mer
(SQEPMSIYVYALPLKMLNIPSINVHHYP;
SEQ ID NO: 1)

MUC1-SEA domain-derived 32 mer
(SEA1;
SPQLSTGVSFFFLSFHISNLQFNSSLEDPSTD-amide;
the amino acid sequence of
which is set forth in
SEQ ID NO: 56,
with a C-terminal amidation)

MUC1-SEA domain-derived 39 mer
(SEA2; STDYYQELQRDISEMFLQIYKQGGFLGLSNI
KFRPGSVV-amide; SEQ ID
NO: 6 with a C-terminal amidation)

HER2 p146-174 29 mer
(TEILKGGVLIQRNPQLCYQDTILWKDIFH;
SEQ ID NO: 13)

HER2 p848-865 21 mer
(DLAARNVLVKSPNHVKITDFG; SEQ ID NO: 29)

HER2 p675-703 29 mer
(IKRRQQKIRKYTMRRLLQETELVEPLTPS;
SEQ ID NO: 24)

HER2 p776-797 22 mer
(GVGSPYVSRLLGICLTSTVQLV; SEQ ID NO: 57)
```

MUC1-VNTR 24mer (AHGVTSAPDTRPAPGSTAP-PAHGV-amide; the amino acid sequence of which is set forth in SEQ ID NO:58, with a C-terminal amidation) also was synthesized as a control for its contrastingly low predicted affinities for HLA-DR and A2.1 (FIG. 3). All peptides were produced to >98% homogeneity as confirmed by mass spectroscopy.

Figures 4A, 4B:
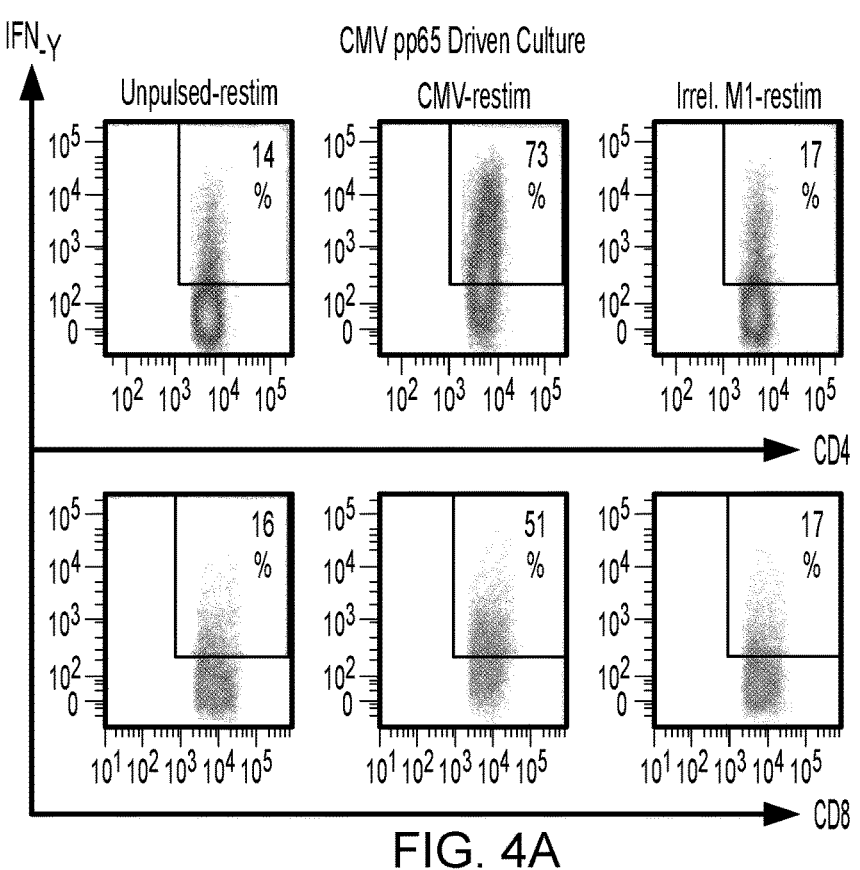
FIG. 4A is a dot plot from an intracellular cytokine assay, plotting interferon gamma (IFNγ) levels of T-cells in response to different restimulatory conditions after T-cell cultures were initially stimulated with the CMV pp65 polypeptide. To control for background levels of IFNγ, T-cells were tested against a lack of polypeptide or an irrelevant MUC1 polypeptide.
FIG. 4B is a dot plot from an intracellular cytokine assay plotting IFNγ levels of T-cells in response to different restimulatory conditions after T-cell cultures were initially stimulated with the SEA2 polypeptide. To control for background levels of IFNγ, T-cells were tested against a lack of polypeptide or an irrelevant CMV and irrelevant MUC1 polypeptide.
Figure 4C:
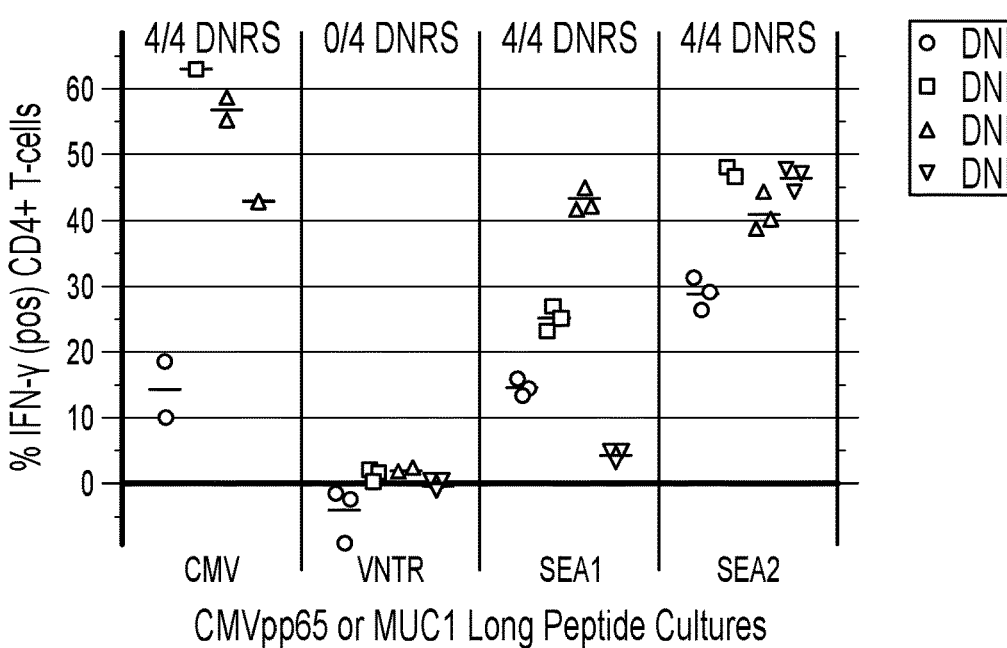
FIGS. 4C and 4D are graphs plotting the frequency of antigen-specific CD4+ T cells and CD8+ T cells, respectively, as measured by the percentage of T-cells, which secrete antigen-specific IFNγ. Briefly, T-cell cultures from four different healthy donors were initially stimulated with one of four polypeptides, CMV pp65, VNTR1, SEA1, or SEA2. At the end of culture, T-cells were restimulated with the original polypeptide and other irrelevant polypeptides or no polypeptide. Each data point represents the level of IFNγ after subtracting the levels of IFNγ from restimulation with irrelevant polypeptides or no polypeptide from levels when T-cells were restimulated with the original polypeptide.
Figure 4D:
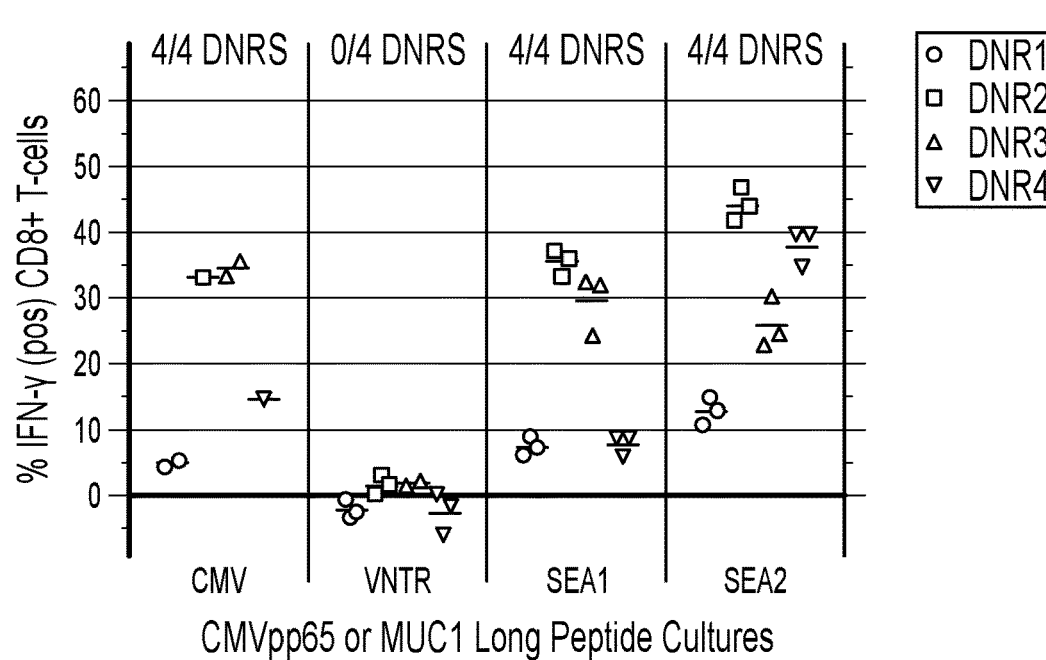
Figures 5A, 5B:
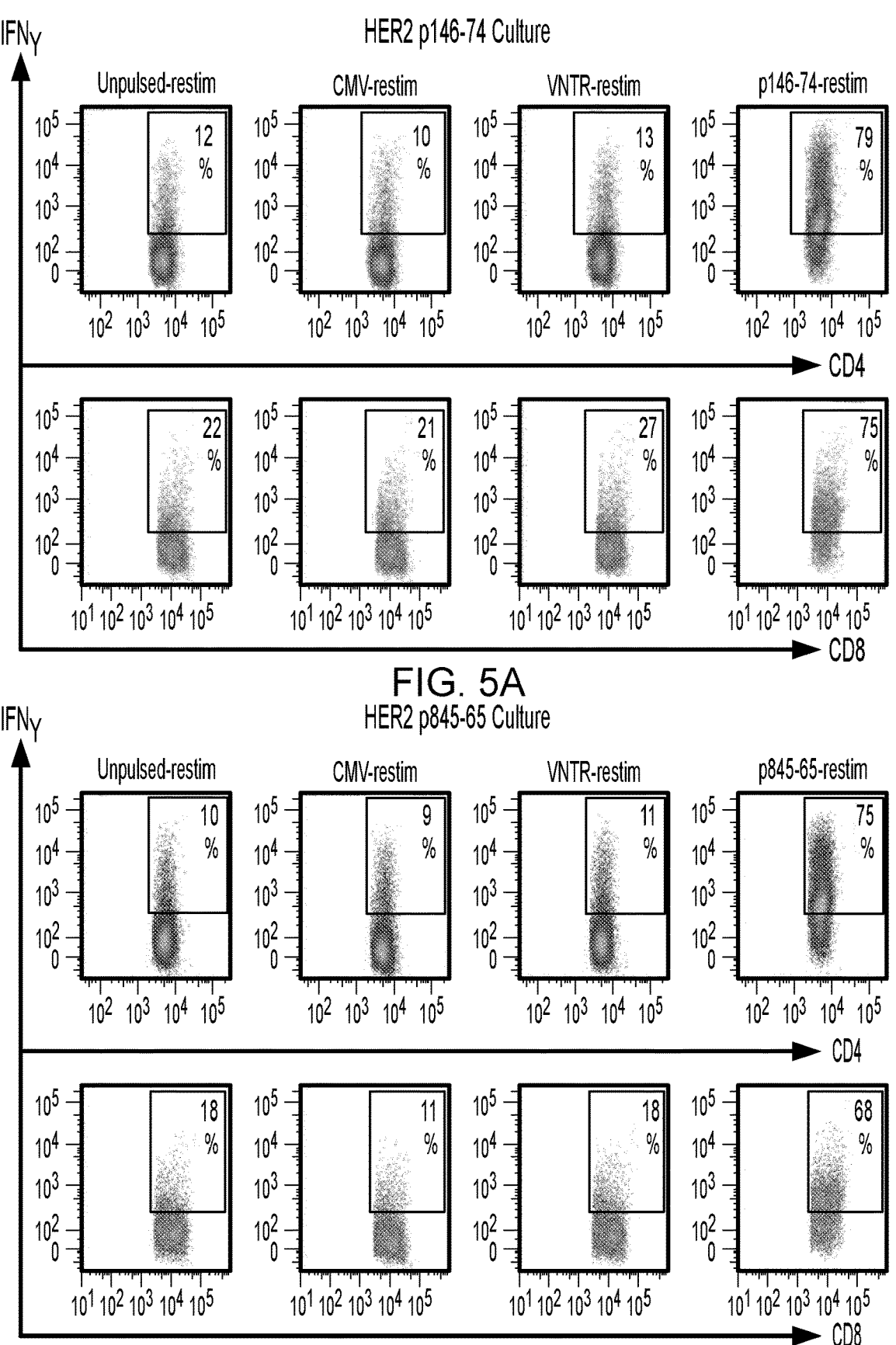
FIG. 5A is a dot plot from an intracellular cytokine assay, plotting IFNγ levels of T-cells in response to different restimulatory conditions after T-cell cultures were initially stimulated with the HER2/neu-derived p146-74 peptide sequences.
FIG. 5B is a dot plot from an intracellular cytokine assay, plotting IFNγ levels of T-cells in response to different restimulatory conditions after T-cell cultures were initially stimulated with the HER2/neu-derived p845-65 peptide sequences.
Figures 5C, 5D:
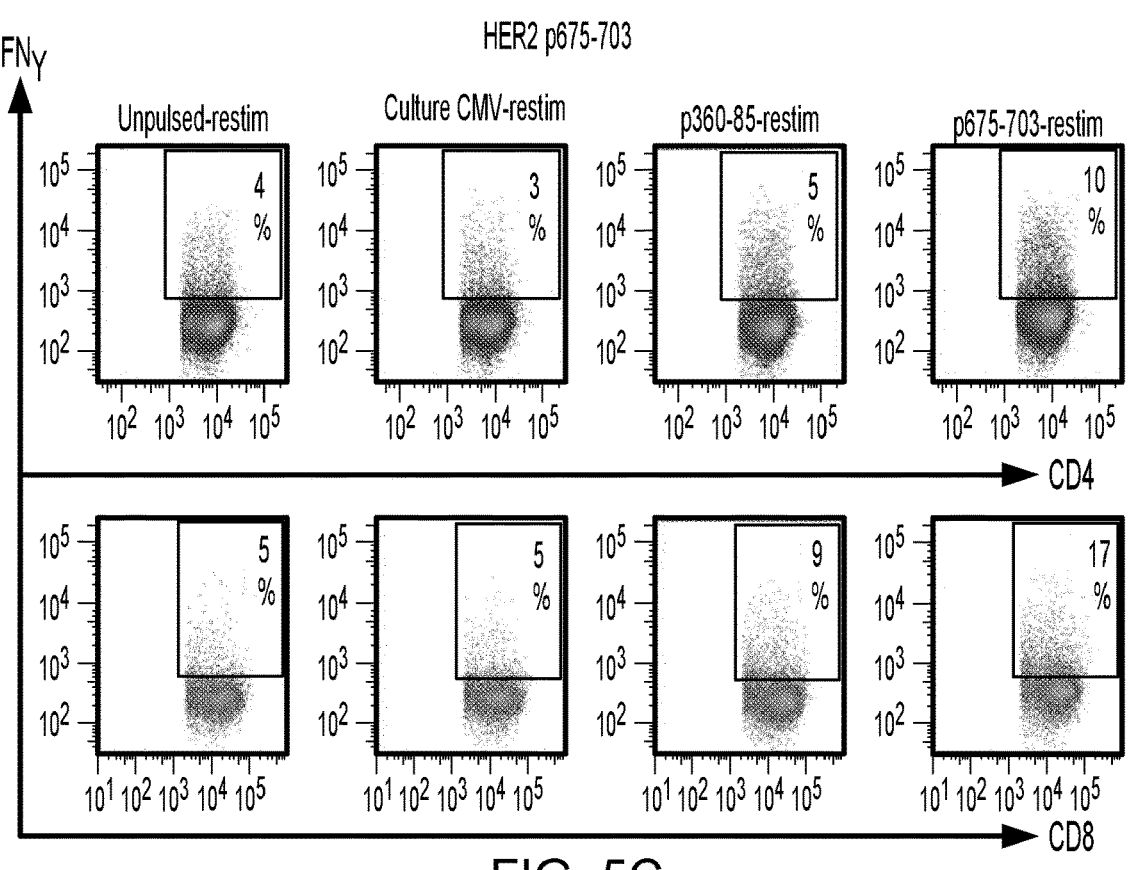
FIG. 5C is a dot plot from an intracellular cytokine assay, plotting IFNγ levels of T-cells in response to different restimulatory conditions after T-cell cultures were initially stimulated with the HER2/neu-derived p675-703 peptide sequences.
FIG. 5D is a dot plot from an intracellular cytokine assay, plotting IFNγ levels of T-cells in response to different restimulatory conditions after T-cell cultures were initially stimulated with the HER2/neu-derived p776-97 peptide sequences.

The synthesized long peptides were individually pulsed onto GM+R848+LPS conditioned PBMC cultures established from unvaccinated HLA-A2.1+ healthy volunteers, then expanded in rhIL-7 or rhIL-7+rhIL-2. Within 16 culture days, it was consistently possible to numerically expand and significantly increase the frequency of T-cells with natural specificity for MUC1, HER2, or CMV, both CD4+ and CD8+(FIGS. 4A, 4B, and 5A-5D). The SEA1 and SEA2 MUC1 sequences as well as CMVpp65 were highly immunogenic, whereas the VNTR non-glycosylated sequence was reproducibly less effective (FIGS. 4C and 4D). Proliferation of CD4+ and CD8$^+$ T-cells was indistinguishable, with both subsets retaining their initial proportionality during expansion.

Figure 6:
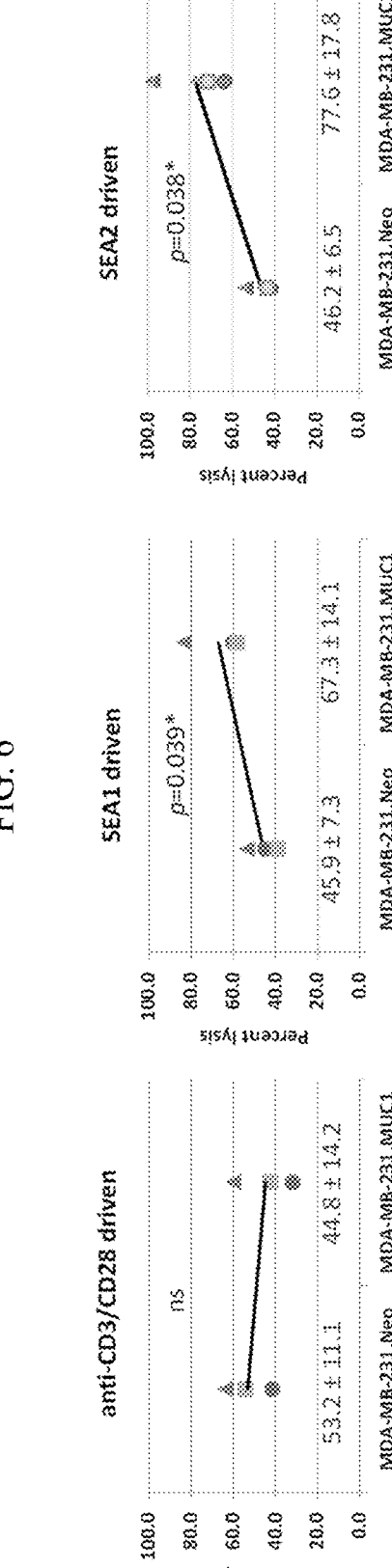
FIG. 6 is a series of graphs plotting percentage of lysis in T-cells from cultures driven polyclonally with anti-CD3/CD28 (left), driven by long peptides sequenced from the SEA1 domain of MUC1 (middle), or driven by long peptides sequenced from the SEA2 domain of MUC1 (right). At the end of T-cell culture expansion, each of the T-cell groups was transduced to express MUC1 (MDA-MB-231.MUC1) or Neo control (MDA-MB-231.Neo). SEA1- and SEA2-driven T-cells from all 3 donors (represented by triangles, circles, or squares) lysed MDA-MB-231.MUC1 targets significantly more than MDA-MB-231.Neo targets (two-tailed p=0.039 and 0.038 applying Student's paired t-test).

T-cells from GM+R848+LPS conditioned PBMC driven by either SEA2 or SEA1 long peptides not only specifically recognized one or both of these sensitizing peptides at restimulation, but also preferentially lysed the HLA-A2.1+ human breast cancer line MDA-MB-231 transduced to express MUC1 (MDA-MB-231.MUC1) compared to MDA-MB-231.Neo control targets. In contrast, polyclonally propagated PBMC T-cells (driven by anti-CD3/anti-CD28) failed to preferentially lyse MDA-MB-231.MUC1 over MDA-MB-231.Neo (FIG. 6). % Lysis was calculated as ((Experimental Lysis-Spontaneous Cr$^{51}$ release)/(Complete Lysis in Triton X-100-Spontaneous Cr$^{51}$ release))×100. % lysis of MDA-MB-231.Neo was statistically indistinguishable for all 3 donors whether cultures were polyclonally-, SEA1- or SEA2-driven. Polyclonally driven T-cells from all 3 donors lysed MDA-MB-231.MUC1 indistinguishably from MDA-MB-231.Neo. In contrast, SEA1- and SEA2-driven T-cells from all 3 donors lysed MDA-MB-231.MUC1 targets significantly more than MDA-MB-231.Neo targets (two-tailed p-0.039 and 0.038 applying Student's paired t-test).

Figure 7:
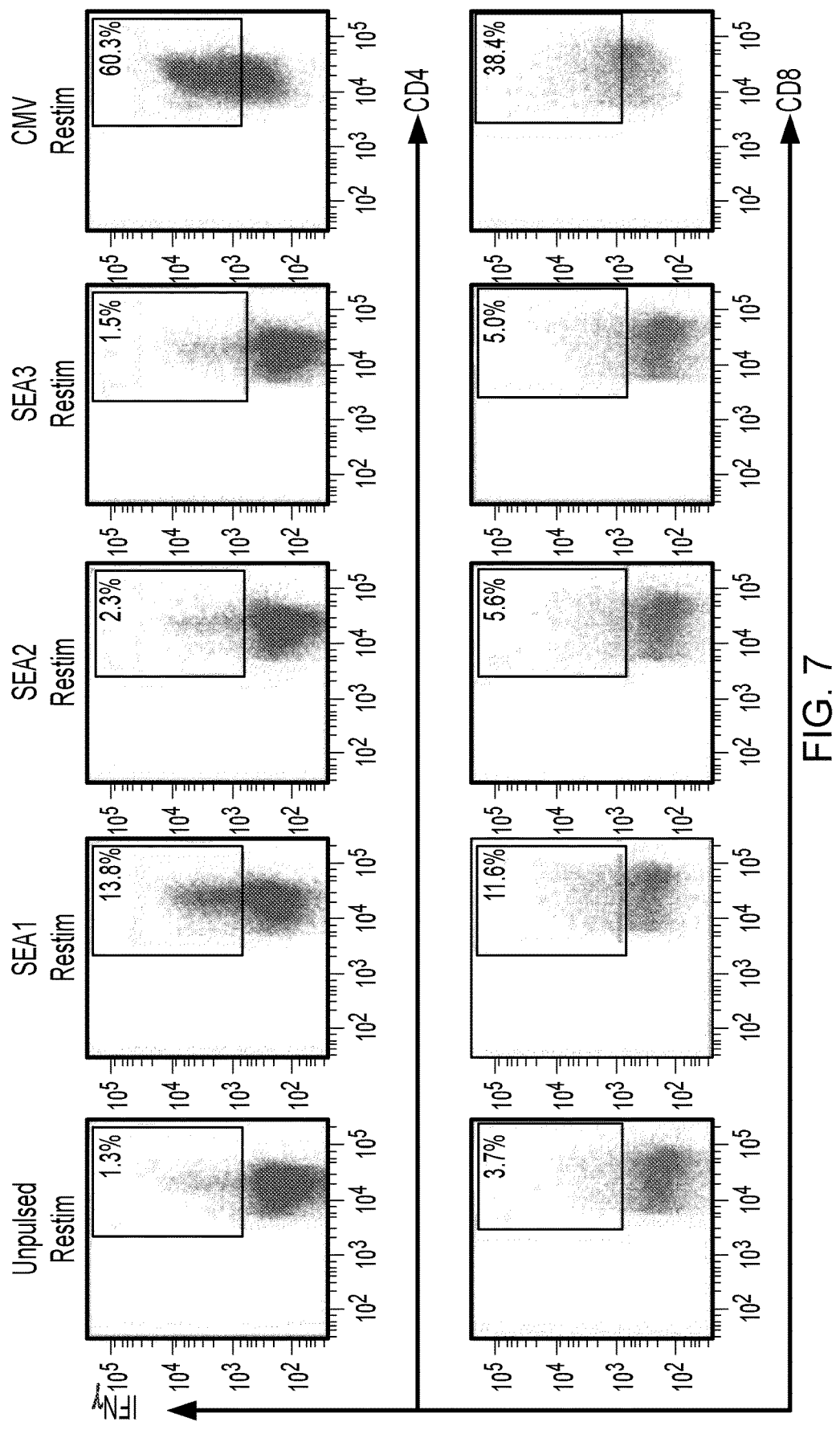
FIG. 7 is a series of dot plots from intracellular cytokine assays, plotting IFNγ levels of T-cells cultured from unfractionated PBMC from a patient with advanced breast cancer in response to different restimulatory conditions (unpulsed, or pulsed with a cocktail of SEA1, SEA2, SEA3, or CMV peptides).

Preliminary PBMC cultures established from four breast cancer patients indicated that the presently described culture system could be applied successfully to patients with malignancies (FIG. 7). Furthermore, cultures could be conducted in expansile 1 liter vessels at least as effectively as in 24 well cluster plates, and cocktails of long peptides could be employed to simultaneously expand T-cells encompassing a variety of oncoprotein specificities (FIG. 7). Furthermore, T-cells cryopreserved at the end of culture fully retained their capacity for Ag-specific IFNγ production upon subsequent re-thaw.

These results demonstrated that the cocktail sensitized and expanded the patient's T-cells to recognize each of the antigens in the cocktail.

Example 3—Preservation of T-Cell Antigen-Specific IFNγ Secretion

Whether PBMC-derived human T-cells retained their facility for secreting Ag-specific IFNγ after recryopreservation at culture's end was examined.

PBMCs cryopreserved at the time of initial collection were thawed, activated with GM-CSF, pulsed with CMVpp65 or SEA1 peptides, exposed to R848 and LPS, and then expanded to Day 19 in culture with IL-7. T-cells were harvested on Day 19, and half the cells were recryopreserved for 4 hours and re-thawed later that day. "Fresh" vs "Recryopreserved" T-cells were compared in a restimulatory intracellular IFNγ cytokine assay. Each bar shows % of CD4+ or CD8+ T-cells making IFNγ upon specific reexposure to CMVpp65 or SEA1 (subtracting background % IFNγ in the absence of Ag reexposure).

Figures 8, 9:
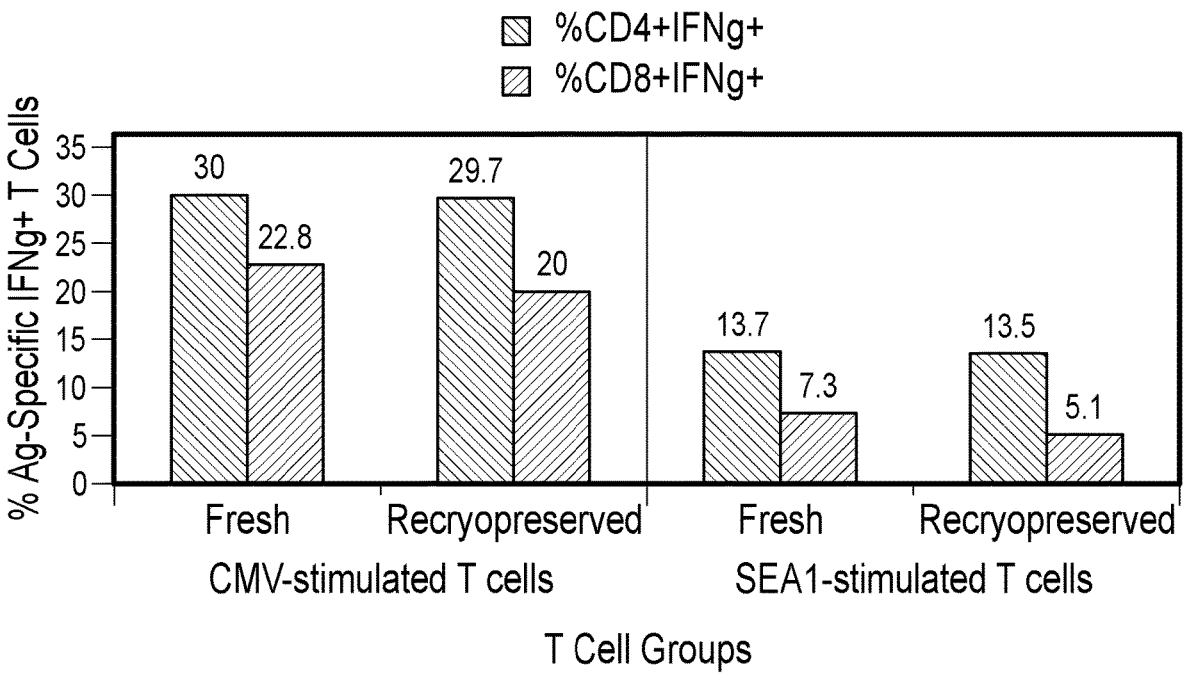
FIG. 8 is a graph plotting the percentage of antigen (Ag) specific IFNγ T cells in fresh and recryopreserved T cells stimulated with either CMVpp65 or SEA1 peptides. The percentage of CD4+ and CD8+ T-cells making IFNγ upon specific reexposure to CMVpp65 or SEA1 is shown. Data is representative of three biological replicates.
FIG. 9 is a graph plotting the percentage of Ag-specific IFNγ T cells stimulated with different concentrations of SEA1 peptides with (SEA1-amide) or without C-terminal amidation.

As shown in FIG. 8, the T-cells can be recryopreserved at the end of culture expansion and still react specifically to the sensitizing peptides after they are re-thawed. Thus, already expanded T-cells can be stored recryopreserved for future therapy.

These results demonstrated that culture-expanded T-cells can be cryopreserved for future therapeutic use without losing their ability to secrete IFNγ upon reexposure to the activating antigen.

Example 4—Modification of Long Polypeptides

The effect of post-translational modification on long polypeptides was examined.

Amidated polypeptides were amidated at the C-terminus as described elsewhere (see, e.g., Brinckerhoff et al., *Int. J. Cancer* 83 (3): 326-34 (1999)).

For the healthy donor shown in FIG. 9, amidation of the SEA1 C-terminus (SEA1-amide) rendered it far superior for sensitizing SEA1-specific CD4+IFNγ-producing T-cells when this donor's PBMC were conditioned in a standard way with GM-CSF, R848, LPS and IL-7 (FIG. 9). The SEA1-specific CD8+ T-cell response was less affected by amidation. A cocktail of peptides such as SEA1, SEA1-amide, acetyl-SEA1 and acetyl-SEA1-amide can be used to capture a broadened SEA1 response (or similarly for any other peptide).

These results demonstrated that amide modification of the C-terminus can modify the immunogenicity of an antigenic polypeptide.

Example 5—Use of Long Polypeptides Having Promiscuous MHC Binding Capabilities to Treat Cancer Patients are diagnosed with Stage III breast cancer that is MUC1 positive. Following surgery and appropriate chemotherapy and/or radiation, the patients are given a vaccine containing at least one MUC1 polypeptide described herein (e.g., SEQ ID NOs:2-7) and a TLR-agonist. Examples of TLR-agonists included, without limitation, CpG, aluminum sulfate, aluminum phosphate, MF59, Pam3CSK4, LPS, polyIC, imiquimod, and R848.

Before, during, and after vaccination, a small amount of the patients' blood optionally is harvested through venipuncture to confirm the efficacy of the vaccine. In some cases, the patients are given an anti-PD-1 antibody or an anti-PD-L1 antibody to prevent a robust immune response against the tumor cells from being inhibited. After treatment, the patients are followed for about 10 years to confirm a lack of recurrence.

If recurrence occurs (e.g., metastasis to bones and lungs), white blood cells are withdrawn via leukophoresis, and the patient's T cells are trained and grown at high numbers outside of the body to recognize one or more MUC1 polypeptides described herein. These T cells are then re-infused into the patient to treat the patient's re-occurring cancer. In some cases, the patient is given an anti-PD-1 antibody or an anti-PD-L1 antibody to prevent a robust immune response against the tumor cells from being inhibited.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated polypeptide, wherein the amino acid sequence of said polypeptide is as set forth in any one of SEQ ID NOs:1-58, and wherein said polypeptide is amidated at the C-terminus.

2. An isolated polypeptide, wherein the amino acid sequence of said polypeptide is as set forth in any one of SEQ ID NOs:1-58, and wherein said polypeptide is acetylated at the N-terminus.

3. A composition comprising at least one isolated polypeptide and an adjuvant, wherein the amino acid sequence of said at least one polypeptide is as set forth in any one of SEQ ID NOs:1-58, and wherein said adjuvant is CpG, aluminum sulfate, aluminum phosphate, MF59, Pam3CSK4, LPS, polyIC, imiquimod, or R848.

4. The composition of claim 3, wherein said polypeptide is amidated at the C-terminus and/or acetylated at the N-terminus.

5. The composition of claim 3, wherein said adjuvant is aluminum sulfate or aluminum phosphate.

6. A method of treating cancer or a precancerous condition in a mammal, wherein said method comprises administering to said mammal a composition comprising an adjuvant and at least one polypeptide, wherein the amino acid sequence of said polypeptide is as set forth in any one of SEQ ID NOs:1-58, and wherein said adjuvant is CpG, aluminum sulfate, aluminum phosphate, or MF59.

7. The method of claim 6, wherein said mammal is a human.

8. The method of claim 6, wherein said method comprises treating said cancer, and wherein said cancer is breast cancer, pancreatic cancer, ovarian cancer, stomach cancer, lung cancer, colon cancer, multiple myeloma, leukemia, brain cancer, or melanoma cancer.

9. The method of claim 6, wherein said method comprises treating said precancerous condition, and wherein said precancerous condition is primary myelofibrosis, essential thrombocythemia, or polycythemia vera.

10. The method of claim 6, wherein said adjuvant is aluminum sulfate or aluminum phosphate.

11. The method of claim 6, wherein said polypeptide is amidated at the C-terminus and/or acetylated at the N-terminus.

12. A vaccine comprising an adjuvant and at least one polypeptide, wherein the amino acid sequence of said polypeptide is as set forth in any one of SEQ ID NOs:1-58, and wherein said adjuvant is CpG, aluminum sulfate, aluminum phosphate, or MF59.

13. The vaccine of claim 12, wherein said adjuvant is CpG or MF59.

14. The vaccine of claim 12, wherein said polypeptide is amidated at the C-terminus and/or acetylated at the N-terminus.

15. A method of inducing an immune response against at least one polypeptide, wherein the sequence of said polypeptide is as set forth in any one of SEQ ID NOs:1-58, wherein said method comprises administering a composition comprising said polypeptide and an adjuvant to a mammal in an amount effective to induce an immune response against said polypeptide, wherein said adjuvant is CpG, aluminum sulfate, aluminum phosphate, or MF59.

16. The method of claim 15, wherein said adjuvant is aluminum sulfate or aluminum phosphate.

17. The method of claim 15, wherein said adjuvant is CpG or MF59.

18. The method of claim 15, wherein said polypeptide is amidated at the C-terminus and/or acetylated at the N-terminus.

19. A method of treating cancer or a precancerous condition in a mammal, wherein said method comprises con-tacting T-cells obtained from said mammal with at least one polypeptide set forth in any one of SEQ ID NOs:1-58 to activate said T-cells, and administering said activated T-cells to said mammal.

20. The method of claim 19, wherein said mammal is a human.

21. The method of claim 19, wherein said method comprises treating cancer, and wherein said administering reduces the number of cancer cells within said mammal.

22. The method of claim 21, wherein said cancer is breast cancer, pancreatic cancer, ovarian cancer, stomach cancer, lung cancer, colon cancer, multiple myeloma, leukemia, brain cancer, or melanoma cancer.

23. The method of claim 19, wherein said method comprises treating said precancerous condition, and wherein said administering reduces a symptom of said precancerous condition within said mammal.

24. The method of claim 23 wherein said precancerous condition is primary myelofibrosis, essential thrombocythemia, or polycythemia vera.

25. The method of claim 19, further comprising expanding said activated T-cells prior to administering said activated T-cells to said mammal.

26. A method of treating cancer or a precancerous condition in a mammal, wherein said method comprises administering activated T-cells to said mammal, wherein said activated T-cells are T-cells that were obtained from said mammal and contacted with at least one polypeptide to activate said T-cells, wherein the amino acid sequence of said polypeptide is as set forth in any one of SEQ ID NOs:1-58.

27. The method of claim 26, wherein said mammal is a human.

28. The method of claim 26, wherein said method comprises treating cancer, and wherein said administering reduces the number of cancer cells within said mammal.

29. The method of claim 28, wherein said cancer is breast cancer, pancreatic cancer, ovarian cancer, stomach cancer, lung cancer, colon cancer, multiple myeloma, leukemia, brain cancer, or melanoma cancer.

30. The method of claim 26, wherein said method comprises treating said precancerous condition, and wherein said administering reduces a symptom of said precancerous condition within said mammal.

31. The method of claim 30 wherein said precancerous condition is primary myelofibrosis, essential thrombocythemia, or polycythemia vera.

32. The method of claim 26, wherein said activated T-cells were expanded prior to being administering to said mammal.

* * * * *

SEQUENCE LISTING

```
Sequence total quantity: 79
SEQ ID NO: 1            moltype = AA  length = 28
FEATURE                Location/Qualifiers
REGION                 1..28
                       note = immunogenic polypeptide
source                 1..28
                       mol_type = protein
                       organism = synthetic construct
SEQUENCE: 1
SQEPMSIYVV ALPLKMLNIP SINVHHYP                                    28

SEQ ID NO: 2            moltype = AA  length = 32
FEATURE                Location/Qualifiers
REGION                 1..32
                       note = immunogenic polypeptide
source                 1..32
                       mol_type = protein
                       organism = synthetic construct
SEQUENCE: 2
VPSSTEKNAV SMTSSVLSSH SPGSGSSTTQ GQ                               32

SEQ ID NO: 3            moltype = AA  length = 30
FEATURE                Location/Qualifiers
REGION                 1..30
                       note = immunogenic polypeptide
source                 1..30
                       mol_type = protein
                       organism = synthetic construct
SEQUENCE: 3
NRPALGSTAP PVHNVTSASG SASGSASTLV                                  30

SEQ ID NO: 4            moltype = AA  length = 37
FEATURE                Location/Qualifiers
REGION                 1..37
                       note = immunogenic polypeptide
source                 1..37
                       mol_type = protein
                       organism = synthetic construct
SEQUENCE: 4
STAPPVHNVT SASGSASGSA STLVHNGTSA RATTTPA                          37
```

-continued

```
SEQ ID NO: 5                  moltype = AA   length = 34
FEATURE                       Location/Qualifiers
REGION                        1..34
                              note = immunogenic polypeptide
source                        1..34
                              mol_type = protein
                              organism = synthetic construct
SEQUENCE: 5
STSPQLSTGV SFFFLSFHIS NLQFNSSLED PSTD                                34

SEQ ID NO: 6                  moltype = AA   length = 39
FEATURE                       Location/Qualifiers
REGION                        1..39
                              note = immunogenic polypeptide
source                        1..39
                              mol_type = protein
                              organism = synthetic construct
SEQUENCE: 6
STDYYQELQR DISEMFLQIY KQGGFLGLSN IKFRPGSVV                           39

SEQ ID NO: 7                  moltype = AA   length = 34
FEATURE                       Location/Qualifiers
REGION                        1..34
                              note = immunogenic polypeptide
source                        1..34
                              mol_type = protein
                              organism = synthetic construct
SEQUENCE: 7
VHDVETQFNQ YKTEAASRYN LTISDVSVSD VPFP                                34

SEQ ID NO: 8                  moltype = AA   length = 27
FEATURE                       Location/Qualifiers
REGION                        1..27
                              note = immunogenic polypeptide
source                        1..27
                              mol_type = protein
                              organism = synthetic construct
SEQUENCE: 8
MELAALCRWG LLLALLPPGA ASTQVCT                                        27

SEQ ID NO: 9                  moltype = AA   length = 28
FEATURE                       Location/Qualifiers
REGION                        1..28
                              note = immunogenic polypeptide
source                        1..28
                              mol_type = protein
                              organism = synthetic construct
SEQUENCE: 9
PASPETHLDM LRHLYQGCQV VQGNLELT                                       28

SEQ ID NO: 10                 moltype = AA   length = 26
FEATURE                       Location/Qualifiers
REGION                        1..26
                              note = immunogenic polypeptide
source                        1..26
                              mol_type = protein
                              organism = synthetic construct
SEQUENCE: 10
VVQGNLELTY LPTNASLSFL QDIQEV                                         26

SEQ ID NO: 11                 moltype = AA   length = 29
FEATURE                       Location/Qualifiers
REGION                        1..29
                              note = immunogenic polypeptide
source                        1..29
                              mol_type = protein
                              organism = synthetic construct
SEQUENCE: 11
LSFLQDIQEV QGYVLIAHNQ VRQVPLQRL                                      29

SEQ ID NO: 12                 moltype = AA   length = 29
FEATURE                       Location/Qualifiers
REGION                        1..29
                              note = immunogenic polypeptide
source                        1..29
                              mol_type = protein
                              organism = synthetic construct
SEQUENCE: 12
AHNQVRQVPL QRLRIVRGTQ LFEDNYALA                                      29
```

-continued

```
SEQ ID NO: 13             moltype = AA   length = 29
FEATURE                   Location/Qualifiers
REGION                    1..29
                          note = immunogenic polypeptide
source                    1..29
                          mol_type = protein
                          organism = synthetic construct
SEQUENCE: 13
TEILKGGVLI QRNPQLCYQD TILWKDIFH                                      29

SEQ ID NO: 14             moltype = AA   length = 33
FEATURE                   Location/Qualifiers
REGION                    1..33
                          note = immunogenic polypeptide
source                    1..33
                          mol_type = protein
                          organism = synthetic construct
SEQUENCE: 14
YQDTILWKDI FHKNNQLALT LIDTNRSRAC HPC                                 33

SEQ ID NO: 15             moltype = AA   length = 23
FEATURE                   Location/Qualifiers
REGION                    1..23
                          note = immunogenic polypeptide
source                    1..23
                          mol_type = protein
                          organism = synthetic construct
SEQUENCE: 15
LGMEHLREVR AVTSANIQEF AGC                                            23

SEQ ID NO: 16             moltype = AA   length = 26
FEATURE                   Location/Qualifiers
REGION                    1..26
                          note = immunogenic polypeptide
source                    1..26
                          mol_type = protein
                          organism = synthetic construct
SEQUENCE: 16
NIQEFAGCKK IFGSLAFLPE SFDGDP                                         26

SEQ ID NO: 17             moltype = AA   length = 26
FEATURE                   Location/Qualifiers
REGION                    1..26
                          note = immunogenic polypeptide
source                    1..26
                          mol_type = protein
                          organism = synthetic construct
SEQUENCE: 17
VFETLEEITG YLYISAWPDS LPDLSV                                         26

SEQ ID NO: 18             moltype = AA   length = 29
FEATURE                   Location/Qualifiers
REGION                    1..29
                          note = immunogenic polypeptide
source                    1..29
                          mol_type = protein
                          organism = synthetic construct
SEQUENCE: 18
DLSVFQNLQV IRGRILHNGA YSLTLQGLG                                      29

SEQ ID NO: 19             moltype = AA   length = 28
FEATURE                   Location/Qualifiers
REGION                    1..28
                          note = immunogenic polypeptide
source                    1..28
                          mol_type = protein
                          organism = synthetic construct
SEQUENCE: 19
TLQGLGISWL GLRSLRELGS GLALIHHN                                       28

SEQ ID NO: 20             moltype = AA   length = 23
FEATURE                   Location/Qualifiers
REGION                    1..23
                          note = immunogenic polypeptide
source                    1..23
                          mol_type = protein
                          organism = synthetic construct
SEQUENCE: 20
```

-continued

```
ELGSGLALIH HNTHLCFVHT VPW                                              23

SEQ ID NO: 21           moltype = AA  length = 21
FEATURE                 Location/Qualifiers
REGION                  1..21
                        note = immunogenic polypeptide
source                  1..21
                        mol_type = protein
                        organism = synthetic construct
SEQUENCE: 21
HNTHLCFVHT VPWDQLFRNP H                                                21

SEQ ID NO: 22           moltype = AA  length = 21
FEATURE                 Location/Qualifiers
REGION                  1..21
                        note = immunogenic polypeptide
source                  1..21
                        mol_type = protein
                        organism = synthetic construct
SEQUENCE: 22
PSGVKPDLSY MPIWKFPDEE G                                                21

SEQ ID NO: 23           moltype = AA  length = 22
FEATURE                 Location/Qualifiers
REGION                  1..22
                        note = immunogenic polypeptide
source                  1..22
                        mol_type = protein
                        organism = synthetic construct
SEQUENCE: 23
EQRASPLTSI ISAVVGILLV VV                                               22

SEQ ID NO: 24           moltype = AA  length = 29
FEATURE                 Location/Qualifiers
REGION                  1..29
                        note = immunogenic polypeptide
source                  1..29
                        mol_type = protein
                        organism = synthetic construct
SEQUENCE: 24
IKRRQQKIRK YTMRRLLQET ELVEPLTPS                                        29

SEQ ID NO: 25           moltype = AA  length = 28
FEATURE                 Location/Qualifiers
REGION                  1..28
                        note = immunogenic polypeptide
source                  1..28
                        mol_type = protein
                        organism = synthetic construct
SEQUENCE: 25
QAQMRILKET ELRKVKVLGS GAFGTVYK                                         28

SEQ ID NO: 26           moltype = AA  length = 26
FEATURE                 Location/Qualifiers
REGION                  1..26
                        note = immunogenic polypeptide
source                  1..26
                        mol_type = protein
                        organism = synthetic construct
SEQUENCE: 26
GVGSPYVSRL LGICLTSTVQ LVTQLM                                           26

SEQ ID NO: 27           moltype = AA  length = 21
FEATURE                 Location/Qualifiers
REGION                  1..21
                        note = immunogenic polypeptide
source                  1..21
                        mol_type = protein
                        organism = synthetic construct
SEQUENCE: 27
DLLNWCMQIA KGMSYLEDVR L                                                21

SEQ ID NO: 28           moltype = AA  length = 21
FEATURE                 Location/Qualifiers
REGION                  1..21
                        note = immunogenic polypeptide
source                  1..21
                        mol_type = protein
                        organism = synthetic construct
```

-continued

```
SEQUENCE: 28
LEDVRLVHRD LAARNVLVKS P                                                      21

SEQ ID NO: 29          moltype = AA  length = 21
FEATURE                Location/Qualifiers
REGION                 1..21
                       note = immunogenic polypeptide
source                 1..21
                       mol_type = protein
                       organism = synthetic construct
SEQUENCE: 29
DLAARNVLVK SPNHVKITDF G                                                      21

SEQ ID NO: 30          moltype = AA  length = 24
FEATURE                Location/Qualifiers
REGION                 1..24
                       note = immunogenic polypeptide
source                 1..24
                       mol_type = protein
                       organism = synthetic construct
SEQUENCE: 30
DGGKVPIKWM ALESILRRRF THQS                                                   24

SEQ ID NO: 31          moltype = AA  length = 19
FEATURE                Location/Qualifiers
REGION                 1..19
                       note = immunogenic polypeptide
source                 1..19
                       mol_type = protein
                       organism = synthetic construct
SEQUENCE: 31
ESILRRRFTH QSDVWSYGV                                                         19

SEQ ID NO: 32          moltype = AA  length = 27
FEATURE                Location/Qualifiers
REGION                 1..27
                       note = immunogenic polypeptide
source                 1..27
                       mol_type = protein
                       organism = synthetic construct
SEQUENCE: 32
RLPQPPICTI DVYMIMVKCW MIDSECR                                                27

SEQ ID NO: 33          moltype = AA  length = 28
FEATURE                Location/Qualifiers
REGION                 1..28
                       note = immunogenic polypeptide
source                 1..28
                       mol_type = protein
                       organism = synthetic construct
SEQUENCE: 33
SECRPRFREL VSEFSRMARD PQRFVVIQ                                               28

SEQ ID NO: 34          moltype = AA  length = 20
FEATURE                Location/Qualifiers
REGION                 1..20
                       note = immunogenic polypeptide
source                 1..20
                       mol_type = protein
                       organism = synthetic construct
SEQUENCE: 34
ARDPQRFVVI QNEDLGPASP                                                        20

SEQ ID NO: 35          moltype = AA  length = 27
FEATURE                Location/Qualifiers
REGION                 1..27
                       note = immunogenic polypeptide
source                 1..27
                       mol_type = protein
                       organism = synthetic construct
SEQUENCE: 35
ALGSLLFLLF SLGWVQPSRT LAGETGQ                                                27

SEQ ID NO: 36          moltype = AA  length = 27
FEATURE                Location/Qualifiers
REGION                 1..27
                       note = immunogenic polypeptide
source                 1..27
                       mol_type = protein
```

-continued

```
                              organism = synthetic construct
SEQUENCE: 36
GLSTERVREL AVALAQKNVK LSTEQLR                                        27

SEQ ID NO: 37          moltype = AA  length = 23
FEATURE                Location/Qualifiers
REGION                 1..23
                       note = immunogenic polypeptide
source                 1..23
                       mol_type = protein
                       organism = synthetic construct
SEQUENCE: 37
LDALPLDLLL FLNPDAFSGP QAC                                            23

SEQ ID NO: 38          moltype = AA  length = 33
FEATURE                Location/Qualifiers
REGION                 1..33
                       note = immunogenic polypeptide
source                 1..33
                       mol_type = protein
                       organism = synthetic construct
SEQUENCE: 38
FLNPDAFSGP QACTRFFSRI TKANVDLLPR GAP                                 33

SEQ ID NO: 39          moltype = AA  length = 44
FEATURE                Location/Qualifiers
REGION                 1..44
                       note = immunogenic polypeptide
source                 1..44
                       mol_type = protein
                       organism = synthetic construct
SEQUENCE: 39
PSTWSVSTMD ALRGLLPVLG QPIIRSIPQG IVAAWRQRSS RDPS                     44

SEQ ID NO: 40          moltype = AA  length = 30
FEATURE                Location/Qualifiers
REGION                 1..30
                       note = immunogenic polypeptide
source                 1..30
                       mol_type = protein
                       organism = synthetic construct
SEQUENCE: 40
PSTWSVSTMD ALRGLLPVLG QPIIRSIPQG                                     30

SEQ ID NO: 41          moltype = AA  length = 34
FEATURE                Location/Qualifiers
REGION                 1..34
                       note = immunogenic polypeptide
source                 1..34
                       mol_type = protein
                       organism = synthetic construct
SEQUENCE: 41
ALRGLLPVLG QPIIRSIPQG IVAAWRQRSS RDPS                                34

SEQ ID NO: 42          moltype = AA  length = 44
FEATURE                Location/Qualifiers
REGION                 1..44
                       note = immunogenic polypeptide
source                 1..44
                       mol_type = protein
                       organism = synthetic construct
SEQUENCE: 42
PSTWSVSTMD ALRGLLPVLG QPIIRSIPQG IVAAWRQRSS RDPS                     44

SEQ ID NO: 43          moltype = AA  length = 29
FEATURE                Location/Qualifiers
REGION                 1..29
                       note = immunogenic polypeptide
source                 1..29
                       mol_type = protein
                       organism = synthetic construct
SEQUENCE: 43
QGYPESVIQH LGYLFLKMSP EDIRKWNVT                                      29

SEQ ID NO: 44          moltype = AA  length = 25
FEATURE                Location/Qualifiers
REGION                 1..25
                       note = immunogenic polypeptide
source                 1..25
```

-continued

```
                          mol_type = protein
                          organism = synthetic construct
SEQUENCE: 44
PEDIRKWNVT SLETLKALLE VNKGH                                   25

SEQ ID NO: 45            moltype = AA  length = 22
FEATURE                  Location/Qualifiers
REGION                   1..22
                          note = immunogenic polypeptide
source                   1..22
                          mol_type = protein
                          organism = synthetic construct
SEQUENCE: 45
NMNGSEYFVK IQSFLGGAPT ED                                      22

SEQ ID NO: 46            moltype = AA  length = 28
FEATURE                  Location/Qualifiers
REGION                   1..28
                          note = immunogenic polypeptide
source                   1..28
                          mol_type = protein
                          organism = synthetic construct
SEQUENCE: 46
SQQNVSMDLA TFMKLRTDAV LPLTVAEV                                28

SEQ ID NO: 47            moltype = AA  length = 27
FEATURE                  Location/Qualifiers
REGION                   1..27
                          note = immunogenic polypeptide
source                   1..27
                          mol_type = protein
                          organism = synthetic construct
SEQUENCE: 47
SQQNVSMDLA TFMKLRTDAV LPLTVAE                                 27

SEQ ID NO: 48            moltype = AA  length = 25
FEATURE                  Location/Qualifiers
REGION                   1..25
                          note = immunogenic polypeptide
source                   1..25
                          mol_type = protein
                          organism = synthetic construct
SEQUENCE: 48
DAVLPLTVAE VQKLLGPHVE GLKAE                                   25

SEQ ID NO: 49            moltype = AA  length = 30
FEATURE                  Location/Qualifiers
REGION                   1..30
                          note = immunogenic polypeptide
source                   1..30
                          mol_type = protein
                          organism = synthetic construct
SEQUENCE: 49
GGIPNGYLVL DLSMQEALSG TPCLLGPGPV                              30

SEQ ID NO: 50            moltype = AA  length = 21
FEATURE                  Location/Qualifiers
REGION                   1..21
                          note = immunogenic polypeptide
source                   1..21
                          mol_type = protein
                          organism = synthetic construct
SEQUENCE: 50
MWMGLIQLVE GVKRKDQGFL E                                       21

SEQ ID NO: 51            moltype = AA  length = 32
FEATURE                  Location/Qualifiers
REGION                   1..32
                          note = immunogenic polypeptide
source                   1..32
                          mol_type = protein
                          organism = synthetic construct
SEQUENCE: 51
GFLEKEFYHK TNIKMRCEFL ACWPAFTVLG EA                           32

SEQ ID NO: 52            moltype = AA  length = 29
FEATURE                  Location/Qualifiers
REGION                   1..29
                          note = immunogenic polypeptide
```

-continued

```
source                   1..29
                         mol_type = protein
                         organism = synthetic construct
SEQUENCE: 52
DQVDWSRLLR DAGLVKMSRK PRASSPLSN                                    29

SEQ ID NO: 53            moltype = AA  length = 40
FEATURE                  Location/Qualifiers
REGION                   1..40
                         note = immunogenic polypeptide
source                   1..40
                         mol_type = protein
                         organism = synthetic construct
SEQUENCE: 53
RRMMRTKMRM RRMRRTRRKM SPARPRTSCR EACLQGWTEA                        40

SEQ ID NO: 54            moltype = AA  length = 24
FEATURE                  Location/Qualifiers
REGION                   1..24
                         note = immunogenic polypeptide
source                   1..24
                         mol_type = protein
                         organism = synthetic construct
SEQUENCE: 54
RRMMRTKMRM RRMRRTRRKM SPAR                                         24

SEQ ID NO: 55            moltype = AA  length = 18
FEATURE                  Location/Qualifiers
REGION                   1..18
                         note = immunogenic polypeptide
source                   1..18
                         mol_type = protein
                         organism = synthetic construct
SEQUENCE: 55
RRMMRTKMRM RRMRRTRR                                                18

SEQ ID NO: 56            moltype = AA  length = 32
FEATURE                  Location/Qualifiers
REGION                   1..32
                         note = immunogenic polypeptide
source                   1..32
                         mol_type = protein
                         organism = synthetic construct
SEQUENCE: 56
SPQLSTGVSF FFLSFHISNL QFNSSLEDPS TD                                32

SEQ ID NO: 57            moltype = AA  length = 22
FEATURE                  Location/Qualifiers
REGION                   1..22
                         note = immunogenic polypeptide
source                   1..22
                         mol_type = protein
                         organism = synthetic construct
SEQUENCE: 57
GVGSPYVSRL LGICLTSTVQ LV                                           22

SEQ ID NO: 58            moltype = AA  length = 24
FEATURE                  Location/Qualifiers
REGION                   1..24
                         note = immunogenic polypeptide
source                   1..24
                         mol_type = protein
                         organism = synthetic construct
SEQUENCE: 58
AHGVTSAPDT RPAPGSTAPP AHGV                                         24

SEQ ID NO: 59            moltype = AA  length = 15
FEATURE                  Location/Qualifiers
REGION                   1..15
                         note = SEA2 epitope
source                   1..15
                         mol_type = protein
                         organism = synthetic construct
SEQUENCE: 59
DYYQELQRDI SEMFL                                                   15

SEQ ID NO: 60            moltype = AA  length = 15
FEATURE                  Location/Qualifiers
REGION                   1..15
```

```
                           note = SEA2 epitope
source                     1..15
                           mol_type = protein
                           organism = synthetic construct
SEQUENCE: 60
YYQELQRDIS EMFLQ                                                    15

SEQ ID NO: 61              moltype = AA  length = 15
FEATURE                    Location/Qualifiers
REGION                     1..15
                           note = SEA2 epitope
source                     1..15
                           mol_type = protein
                           organism = synthetic construct
SEQUENCE: 61
YQELQRDISE MFLQI                                                    15

SEQ ID NO: 62              moltype = AA  length = 15
FEATURE                    Location/Qualifiers
REGION                     1..15
                           note = SEA2 epitope
source                     1..15
                           mol_type = protein
                           organism = synthetic construct
SEQUENCE: 62
DISEMFLQIY KQGGF                                                    15

SEQ ID NO: 63              moltype = AA  length = 15
FEATURE                    Location/Qualifiers
REGION                     1..15
                           note = SEA2 epitope
source                     1..15
                           mol_type = protein
                           organism = synthetic construct
SEQUENCE: 63
ISEMFLQIYK QGGFL                                                    15

SEQ ID NO: 64              moltype = AA  length = 15
FEATURE                    Location/Qualifiers
REGION                     1..15
                           note = SEA2 epitope
source                     1..15
                           mol_type = protein
                           organism = synthetic construct
SEQUENCE: 64
SEMFLQIYKQ GGFLG                                                    15

SEQ ID NO: 65              moltype = AA  length = 15
FEATURE                    Location/Qualifiers
REGION                     1..15
                           note = SEA2 epitope
source                     1..15
                           mol_type = protein
                           organism = synthetic construct
SEQUENCE: 65
EMFLQIYKQG GFLGL                                                    15

SEQ ID NO: 66              moltype = AA  length = 15
FEATURE                    Location/Qualifiers
REGION                     1..15
                           note = SEA2 epitope
source                     1..15
                           mol_type = protein
                           organism = synthetic construct
SEQUENCE: 66
MFLQIYKQGG FLGLS                                                    15

SEQ ID NO: 67              moltype = AA  length = 15
FEATURE                    Location/Qualifiers
REGION                     1..15
                           note = SEA2 epitope
source                     1..15
                           mol_type = protein
                           organism = synthetic construct
SEQUENCE: 67
FLQIYKQGGF LGLSN                                                    15

SEQ ID NO: 68              moltype = AA  length = 15
FEATURE                    Location/Qualifiers
```

```
REGION                  1..15
                        note = SEA2 epitope
source                  1..15
                        mol_type = protein
                        organism = synthetic construct

SEQUENCE: 68
LQIYKQGGFL GLSNI                                           15

SEQ ID NO: 69           moltype = AA  length = 15
FEATURE                 Location/Qualifiers
REGION                  1..15
                        note = SEA2 epitope
source                  1..15
                        mol_type = protein
                        organism = synthetic construct

SEQUENCE: 69
QIYKQGGFLG LSNIK                                           15

SEQ ID NO: 70           moltype = AA  length = 15
FEATURE                 Location/Qualifiers
REGION                  1..15
                        note = SEA2 epitope
source                  1..15
                        mol_type = protein
                        organism = synthetic construct

SEQUENCE: 70
IYKQGGFLGL SNIKF                                           15

SEQ ID NO: 71           moltype = AA  length = 15
FEATURE                 Location/Qualifiers
REGION                  1..15
                        note = SEA2 epitop
source                  1..15
                        mol_type = protein
                        organism = synthetic construct

SEQUENCE: 71
YKQGGFLGLS NIKFR                                           15

SEQ ID NO: 72           moltype = AA  length = 15
FEATURE                 Location/Qualifiers
REGION                  1..15
                        note = SEA2 epitope
source                  1..15
                        mol_type = protein
                        organism = synthetic construct

SEQUENCE: 72
KQGGFLGLSN IKFRP                                           15

SEQ ID NO: 73           moltype = AA  length = 15
FEATURE                 Location/Qualifiers
REGION                  1..15
                        note = SEA2 epitope
source                  1..15
                        mol_type = protein
                        organism = synthetic construct

SEQUENCE: 73
QGGFLGLSNI KFRPG                                           15

SEQ ID NO: 74           moltype = AA  length = 15
FEATURE                 Location/Qualifiers
REGION                  1..15
                        note = SEA2 epitope
source                  1..15
                        mol_type = protein
                        organism = synthetic construct

SEQUENCE: 74
GFLGLSNIKF RPGSV                                           15

SEQ ID NO: 75           moltype = AA  length = 15
FEATURE                 Location/Qualifiers
REGION                  1..15
                        note = SEA2 epitope
source                  1..15
                        mol_type = protein
                        organism = synthetic construct

SEQUENCE: 75
FLGLSNIKFR PGSVV                                           15

SEQ ID NO: 76           moltype = AA  length = 655
```

-continued

```
FEATURE            Location/Qualifiers
source             1..655
                   mol_type = protein
                   organism = Homo sapiens
SEQUENCE: 76
MTPGTQSPFF LLLLLTVLTV VTGSGHASST PGGEKETSAT QRSSVPSSTE KNAVSMTSSV  60
LSSHSPGSGS STTQGQDVTL APATEPASGS AATWGQDVTS VPVTRPALGS TTPPAHDVTS  120
APDNKPAPGS TAPPAHGVTS APDTRPAPGS TAPPAHGVTS APDTRPAPGS TAPPAHGVTS  180
APDTRPAPGS TAPPAHGVTS APDTRPAPGS TAPPAHGVTS APDTRPAPGS TAPPAHGVTS  240
APDTRPAPGS TAPPAHGVTS APDTRPAPGS TAPPAHGVTS APDTRPAPGS TAPPAHGVTS  300
APDTRPAPGS TAPPAHGVTS APDTRPAPGS TAPPAHGVTS APDNRPALGS TAPPVHNVTS  360
ASGSASGSAS TLVHNGTSAR ATTTPASKST PFSIPSHHSD TPTTLASHST KTDASSTHHS  420
SVPPLTSSNH STSPQLSTGV SFFFLSFHIS NLQFNSSLED PSTDYYQELQ RDISEMFLQI  480
YKQGGFLGLS NIKFRPGSVV VQLTLAFREG TINVHDVETQ FNQYKTEAAS RYNLTISDVS  540
VSDVPFPFSA QSGAGVPGWG IALLVLVCVL VALAIVYLIA LAVCQCRRKN YGQLDIFPAR  600
DTYHPMSEYP TYHTHGRYVP PSSTDRDPYE KVSAGNGGSS LSYTNPAVAA ASANL       655

SEQ ID NO: 77          moltype = AA  length = 475
FEATURE            Location/Qualifiers
source             1..475
                   mol_type = protein
                   organism = Homo sapiens
SEQUENCE: 77
MTPGTQSPFF LLLLLTVLTV VTGSGHASST PGGEKETSAT QRSSVPSSTE KNAVSMTSSV  60
LSSHSPGSGS STTQGQDVTL APATEPASGS AATWGQDVTS VPVTRPALGS TTPPAHDVTS  120
APDNKPAPGS TAPPAHGVTS APDTRPAPGS TAPPAHGVTS APDNRPALGS TAPPVHNVTS  180
ASGSASGSAS TLVHNGTSAR ATTTPASKST PFSIPSHHSD TPTTLASHST KTDASSTHHS  240
SVPPLTSSNH STSPQLSTGV SFFFLSFHIS NLQFNSSLED PSTDYYQELQ RDISEMFLQI  300
YKQGGFLGLS NIKFRPGSVV VQLTLAFREG TINVHDVETQ FNQYKTEAAS RYNLTISDVS  360
VSDVPFPFSA QSGAGVPGWG IALLVLVCVL VALAIVYLIA LAVCQCRRKN YGQLDIFPAR  420
DTYHPMSEYP TYHTHGRYVP PSSTDRSPYE KVSAGNGGSS LSYTNPAVAA TSANL       475

SEQ ID NO: 78          moltype = AA  length = 1255
FEATURE            Location/Qualifiers
source             1..1255
                   mol_type = protein
                   organism = Homo sapiens
SEQUENCE: 78
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAGVGSP  780
YVSRLLGICL TSTVQLVTQL MPYGCLLDHV RENRGRLGSQ DLLNWCMQIA KGMSYLEDVR  840
LVHRDLAARN VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID VYMIMVKCWM  960
IDSECRPRFR ELVSEFSRMA RDPQRFVVIQ NEDLGPASPL DSTFYRSLLE DDDMGDLVDA  1020
EEYLVPQQGF FCPDPAPGAG GMVHHRHRSS STRSGGGDLT LGLEPSEEEA PRSPLAPSEG  1080
AGSDVFDGDL GMGAAKGLQS LPTHDPSPLQ RYSEDPTVPL PSETDGYVAP LTCSPQPEYV  1140
NQPDVRPQPP SPREGPLPAA RPAGATLERP KTLSPGKNGV VKDVFAFGGA VENPEYLTPQ  1200
GGAAPQPHPP PAFSPAFDNL YYWDQDPPER GAPPSTFKGT PTAENPEYLG LDVPV       1255

SEQ ID NO: 79          moltype = AA  length = 40
FEATURE            Location/Qualifiers
source             1..40
                   mol_type = protein
                   organism = Homo sp.
SEQUENCE: 79
RRMMRTKMRM RRMRRTRRKM SPARPRTSCR EACLQGWTEA                         40
```